United States Patent
Lianidou et al.

(10) Patent No.: US 12,270,081 B2
(45) Date of Patent: Apr. 8, 2025

(54) METHOD FOR QUANTIFICATION OF PD-L1 EXPRESSION

(71) Applicant: PHARMASSIST LTD, Athens (GR)

(72) Inventors: Evrykleia Lianidou, Athens (GR); Areti Strati, Athens (GR)

(73) Assignee: PHARMASSIST LTD, Athens (GR)

( * ) Notice: Subject to any disclaimer, the term of this patent is extended or adjusted under 35 U.S.C. 154(b) by 112 days.

(21) Appl. No.: 17/399,339

(22) Filed: Aug. 11, 2021

(65) Prior Publication Data

US 2022/0073995 A1 Mar. 10, 2022

Related U.S. Application Data

(62) Division of application No. 15/771,165, filed as application No. PCT/GR2015/000054 on Oct. 27, 2015, now abandoned.

(51) Int. Cl.
C12P 19/34 (2006.01)
C12Q 1/6853 (2018.01)
C12Q 1/6886 (2018.01)

(52) U.S. Cl.
CPC ......... *C12Q 1/6886* (2013.01); *C12Q 1/6853* (2013.01); *C12Q 2600/106* (2013.01); *C12Q 2600/112* (2013.01); *C12Q 2600/118* (2013.01); *C12Q 2600/156* (2013.01); *C12Q 2600/16* (2013.01); *C12Q 2600/166* (2013.01)

(58) Field of Classification Search
CPC .................................................. C12Q 1/6851
See application file for complete search history.

(56) References Cited

U.S. PATENT DOCUMENTS

| | | |
|---|---|---|
| 2007/0213939 A1 | 9/2007 | Liew et al. |
| 2007/0231264 A1 | 10/2007 | de Waal Malefyt et al. |
| 2013/0338035 A1 | 12/2013 | Dressel et al. |
| 2015/0071910 A1 | 3/2015 | Kowanetz et al. |

FOREIGN PATENT DOCUMENTS

| | | |
|---|---|---|
| WO | 2014151006 A2 | 9/2014 |
| WO | 2016/034718 A1 | 3/2016 |

OTHER PUBLICATIONS

Keir, Mary E. et al., "PD-1 and Its Ligands in Tolerance and Immunity", Annual Reviews of Immunology, 26:677-704 (2008).
Callahan, Margaret K. and Wolchok, Jedd D., "At the bedside: CTLA-4- and PD-1-blocking antibodies in cancer immunotherapy", Journal of Leukocyte Biology 94, 1-13 (May 10, 2013).
Larkin, J. et al., "Combined Nivolumab and Ipilimumab or Monotherapy in Untreated Melanoma", New England Journal of Medicine 373, 23-34 (Jul. 2, 2015).
Mazel, Martine et al., "Frequent expression of PD-L1 on circulating breast cancer cells", Molecular Oncology 9, 1773-1782 (2015).
Oliveira-Costa, Joao Paulo et al., "Gene expression patterns through oral squamous cell carcinoma development: PD-L1 expression in primary tumor and circulating tumor cells", Oncotarget,vol. 6, No. 25, p. 20902-20920 (May 15, 2015) (available at www.impactjournals.com/oncotarget/).
Suzuki, Toshihide et al., "Control Selection for RNA Quantitation", BioTechniques, 29:332-337 (Aug. 2000).
Bustin, S.A., "Absolute quantification of mRNA using real-time reverse transcription of polymerase chain reaction assays", Journal of Molecular Endocrinology 25:169-193 (2000).
Cornelis, J.A. et al., "Endpoints in Adjuvant Treatment Trials: A Systematic Review of the Literature in Colon Cancer and Proposed definitions for Future Trials", Journal National Cancer Institute 99:998-1003 (Jul. 4, 2007).
Strati, Areti et al., "Gene expression profile of circulating tumor cells in breast cancer by RT-qPCR", BioMed Central Cancer 11:422, pp. 1-12 (2011).
Geng, Hui et al., "HSP70 vaccine in combination with gene therapy with plasmid DNA encoding sPD-1 overcomes immune resistance and suppresses the progression of pulmonary metastatic melanoma", International Journal of Cancer 118:2657-2664 (2006).
Wu, Yanhua et al., "Link of DIk/ZIP Kinase to cell apoptosis and tumor suppression", Biochemical and Biophysical Research Communications 392:510-515 (2010).
Rychlik, Wojciech and Rhoads, Robert E., "A computer program for choosing optimal oligonucleotides for filter hybridization, sequencing and in vitro amplification of DNA", Nucleic Acids Research, Department of Biochemistry, University of Kentucky 17:543-8551 (1989).

*Primary Examiner* — Kenneth R Horlick
(74) *Attorney, Agent, or Firm* — Finch & Maloney PLLC

(57) ABSTRACT

Disclosed is a method for determining the expression of PD-L1 that is based on a RT-qPCR in a RNA sample of, for example, Circulating Tumor Cells (CTC) or fresh frozen primary tumor tissues. In particular, a method is disclosed for the detection of PD-L1 mRNA positive CTCs or primary tumor tissues (fresh frozen) based on the quantitative determination of the molecular marker (PD-L1) in biological samples of patients suffering from cancer. In use, detection can take place before, during or after immune therapy or any other treatment in order to provide significant information concerning the guiding or the monitoring of the anti-PD-L1 agents effectiveness. This RT-qPCR assay could comprise a promising companion diagnostic test in order to evaluate the PD-L1 expressional status on CTC or tumor tissue, providing clinical applications, which could have an important impact on therapeutic interventions since the expression of PD-L1 is associated with response to immunotherapy.

21 Claims, 9 Drawing Sheets

Specification includes a Sequence Listing.

PD-L1 mRNA sequence

Forward *PD-L1* actgcactttaggagattagatcctgaggaaaaccatacagctgaattggtcatcccag
/
|||||||||||||||||||
cgacttaaccagtagggtc

**Hydrolysis probe *PD-L1*** aactacctctggcacatcctccaaatgaaaggactcacttggtaattctgggagccatct
|| |||||||||||||||||||||||||||||
ttgatggagaccgtgtaggaggtttactttc Reverse *PD-L1* ttc cctcttactacc
||| |||||||||||
tattatgccttggtgtagcactgacattcatcttccgtttaagaaaag/ggagaatgatgg tacacttt
||||||||
atgtgaaaaaatgtggcatccaagatacaaactcaaagaagcaaagtgat

FIG. 2

B2M mRNA sequence

```
                                            Forward B2M
tactacactgaattcaccccactgaaaaagatgagtatgcctgccgtgtgaaccatgt
                                         ||||||||||||||||||||||||
                                         cggacggcacacttggtaca
```

```
                                        Hydrolysis probe B2M
                        caccc tagctctgtacattcgtcgtagtac
                        ||||| ||||||||||||||||||||||||
            gactttgtcacagcccaagatagttaagtggg/atcgagacatgtaagcagcatcatg
```

Reverse B2M

```
ctc caaacttctacggcgtaaa
||| ||||||||||||||||||||
gag/gtttgaagatgccgcatttggattggatgaattccaaattctgctt
```

FIG. 3

METHOD FOR QUANTIFICATION OF PD-L1 EXPRESSION

RELATED APPLICATIONS

This application is a divisional application of U.S. patent application Ser. No. 15/771,165 now abandoned) filed on Apr. 27, 2018, and titled METHOD FOR QUANTIFICATION OF PD-L1 EXPRESSION, which claims the benefit under 35 U.S.C. § 371 as a U.S. National Application of PCT application no. PCT/GR2015/000054, filed on Oct. 27, 2015, the contents of which are incorporated herein by reference in their entireties.

TECHNICAL FIELD

The present invention relates to a highly sensitive, specific and reproducible real time RT-qPCR assay for the quantification of PD-L1 expression in a RNA sample, such as an isolated RNA sample from Circulating Tumor Cells (CTCs) in peripheral blood of patients with solid cancers or fresh frozen primary tumor tissues.

BACKGROUND OF THE INVENTION

The discovery of crucial molecular pathways that promote tumor growth and maintenance together with the development of drugs that specifically inhibit these pathways has changed much in the perennially limited panoply of options to treat many types of cancer. The promise of the emerging field of personalized medicine will increasingly be used to tailor therapeutics to defined sub-populations, and eventually, individual patients in order to enhance efficacy and minimize adverse side effects. However, the success of personalized medicine depends on having accurate, reproducible and clinically useful companion diagnostic tests to identify patients who can benefit from targeted therapies. According to this concept, the most recent paradigm is the successful co-development of a first-in-class selective inhibitor of oncogenic BRAF kinase, vemurafenib (ZELBORAF), which targets only the mutant BRAF protein, which is detected V600E positive by the approved companion diagnostic test, the Cobas 4800 BRAF V600 mutation test (Roche Molecular Diagnostics). Despite the recent development of targeted therapies in many types of cancer, many patients do not benefit from these therapies. This fact led to an improved understanding of the mechanisms of protective anti-tumor immunity and the development of more efficacious immunotherapies that increase patient survival confirming the long-standing idea that immunity plays an important role in cancer pathogenesis. Immunotherapy is a type of cancer treatment designed to boost the body's natural defenses to fight cancer. It uses materials either made by the body or in a laboratory to improve, target, or restore the function of the immune system. It is now evident through intense research efforts that cancer cells can develop specific mechanisms to avoid immunosurveillance. One of these mechanisms is to present itself to the immune system in such a way that it fails to recognize it as something that should be killed. Another mechanism is to interfere with the abilities of T-cells, whose duty it is to carry out such killings and which, by hanging around for decades in the body, provide durable immunity to a given disease. Lastly, there are all sorts of ways in which the immune system as a whole can be suppressed.

Human cancers are characterized by high frequencies of genetic and epigenetic alterations, generating neo-antigens potentially recognizable by the immune system. The ability of the immune system to recognise its normal cells from tumor cells and to attack against foreign invaders such as viruses provides the basis for the rapid and specific clearance of most infections. The immune system is able to detect and eliminate most tumors, which are at an early stage and clinically non-detectable by the concept of cancer immuno-editing. However, the cancer cells use a "cellular camouflage" in order to fool the immune system into thinking that they are normal cells; as a result, some tumors are not completely destroyed and escape from the immune-surveillance. A basic hindrance for immunotherapeutic approaches is that the majority of mechanisms are active at the tumor site, which act together in order to balance effectively the anti-tumor immunity.

Despite the fact that an endogenous immune response to cancer has been observed in patients, this response seems to be ineffective, and the established cancers are tolerated by the immune system. Contributing to this state of tolerance, tumors may exploit several distinct mechanisms to actively suppress the host immune response. Among these mechanisms, endogenous "immune checkpoints" that normally terminate immune responses to mitigate collateral tissue damage can be co-opted by tumors to evade immune destruction. Recently, many specific immune checkpoint pathway inhibitors have been developed and approved by FDA to provide new immunotherapeutic approaches for treating cancer, including the development of the anti-CTLA-4 antibody (Ab), ipilimumab (Yervoy), for the treatment of patients with advanced melanoma and anti-PD-L1 antibody, nivolumab (Opdivo), for the treatment of patients with advanced squamous non-small cell lung cancer (NSCLC) who have progressed on or after platinum-based chemotherapy.

Programmed death 1 (PD-1) is an immune inhibitory receptor expressed on several immune cells, particularly cytotoxic T cells. This receptor interacts with two ligands, programmed death ligand 1 (PD-L1) (B7-H1, CD274) and PD-L2 (B7-DC). The PD-1 has greater affinity for PD-L1, which is widely expressed on tumor cells, as well as other immune cells, while PD-L2 is expressed primarily on macrophages and dendritic cells [Keir M, Butte M, Freeman G, Sharpe A. PD-1 and its ligands in tolerance and immunity. Annu Rev Immunol 2008; 26: 677-704]. When PD-1 binds to tumor cells expressing PD-L1, T-cell activity and cytokine production are suppressed, leading to T-cell exhaustion. PD-L1 ligation with PD-1 during infection or inflammation in normal tissues is critically important in maintaining homeostasis of immune response to prevent autoimmunity. The PD-1/PD-L1 interaction in the tumor microenvironment, however, provides an immune escape for tumor cells by turning off cytotoxic T cells. Thus, by blocking this interaction, it is expected that tumor cells will be attacked by cytotoxic T cells. The activation of the PD-1/PD-L1 pathway protects tumor cells from immunological responses mediated by T-cells. Inhibition of the PD-1/PD-L1 pathway reverses immune evasion by replenishing a plethora of activated non-exhausted T-cells. The development and clinical testing of immune blocking antibodies has resulted in until now clinical activity in a variety of malignancies including melanoma and lung cancer [Callahan M K, Wolchok J D. At the bedside: CTLA-4 and PD-1-blocking antibodies in cancer immunotherapy. J Leukoc Biol. 2013; 94: 41-53].

Most recently, Larkin et al., presented a randomized, double-blind, phase 3 study, in which the nivolumab (anti-PD-1 antibody) as monotherapy or the combination nivolumab plus ipilimumab (anti-CTLA-4 antibody) were compared to ipilmumab alone in patients with metastatic melanoma. The median progression-free survival was longer with nivolumab plus ipilimumab, as compared with ipilimumab or nivolumab as monotherapy. However, in patients with PD-L1-positive tumors, the median progression-free survival (PFS) was 14.0 months in the nivolumab-plus-ipilimumab group and in the nivolumab group, but in patients with PD-L1-negative tumors, PFS was longer with the combination therapy than with nivolumab alone. From these results it has become clear that the expression of PD-L1 seems to be a significant predictive biomarker in anti-PD-L1 treatments. Thus, the need for developing a new companion diagnostic test for detecting PD-L1 positive or negative tumors, is increasing [Larkin J, Chiarion-Sileni V, Gonzalez R, Grob J J, Cowey C L, Lao C D, et al. Combined Nivolumab and Ipilimumab or Monotherapy in Untreated Melanoma. N Engl J Med. 2015; 373: 23-34].

Recently, the "liquid biopsy" approach has a high potential to change significantly the therapeutic strategy in patients suffering from many types of cancer. The detection, enumeration and the molecular characterization of Circulating Tumor Cells (CTCs), cell-free circulating tumor DNA (ctDNA) and circulating microRNAs (miRNAs) provide an extremely powerful and reliable non-invasive source of blood-based biomarkers for the individual molecular profiling of each patient in real time, and especially before and after treatment. The applications of liquid biopsy are based on the identification of molecular targets, the assessment of prognosis, the diagnosis of recurrence/progression, the monitoring of response to therapy and monitoring of tumor genomic profiles in real time. Most importantly, these blood-based tests seem to be very challenging and highly important in case that tumor biopsies are not accessible (such as in the case of NSCLC). Moreover, they can offer a close follow-up of disease biomarkers enabling the monitoring of the efficacy of treatment and potentially improve the choice of treatment options.

Recently, Mazel et al., using the CellSearch™ system (Veridex, J&J), an FDA-cleared platform for CTCs enumeration, by using an anti-PD-L1 specific antibody and the fourth channel for imaging in the CellSearch, found PD-L1 positive CTCs in 11 out of 16 (68.8%) patients with metastatic breast cancer. More specifically, in their study, they have used the anti-human B7-H1/PD-L1PE-conjugated monoclonal antibody for PD-L1 expression, suggesting that this assay could be used for liquid biopsy for monitoring and stratification of cancer patients undergoing immune checkpoint blockade [Mazel M, Jacot W, Klaus P, Bartkowiak K, Topart D, Cayrefourcq L et al. Frequent expression of PD-L1 on circulating breast cancer cells. Mol Oncol. 2015, Article in press]. Moreover, Oliveira-Costa et al., found a strong cytoplasmatic expression of PD-L1 in CTCs in oral squamous cell carcinoma using immunofluorescence and Nanostring [Oliveira-Costa J P, Fiorini de Carvalho A, Gobbi da Silveira G, Amaya P, Wu Y et al., Gene expression patterns through oral squamous cell carcinoma development: PD-L1 expression in primary tumor and circulating tumor cells. Oncotarget. 2015; 6: 20902-20].

The detection of PD-L1 expression in CTCs in a quantitative way could be used for monitoring the efficacy of immune checkpoint inhibitors as a "liquid biopsy" approach and could offer many advances in clinical practice. Thus, for this reason, an ultrasensitive and highly specific RT-qPCR based method for the quantification of PD-L1 expression in CTCs was developed and validated, suitable for monitoring the efficacy of checkpoint inhibitors in peripheral blood of cancer patients. This assay has a very high analytical sensitivity and specificity in order to quantify the expression of PD-L1 in CTCs, and is highly sensitive in comparison to other methods used in tumor tissues such as immunohistochemistry. Moreover, the developed method is a closed tube molecular diagnostic test that comprises a simple and high throughput clinical tool, which can easily be automated and used in most molecular diagnostic clinical laboratories since it does not require expensive instrumentation, and is easy to use. Moreover, the developed method is quantitative, thus enabling not only to recognize differences in the expression of PD-L1 in clinical samples, but moreover to be subjected to daily quality control performance tests (robustness, reproducibility, within-run and between-run precision) that are very important for accreditation purposes.

For the first time a novel RT-qPCR based method with novel specifically designed primers and a hydrolysis probe for the quantification of PD-L1 mRNA transcripts in a human clinical sample and especially in peripheral blood (CTCs) was designed. Especially for CTCs molecular characterization, highly sensitive, robust and specific methodologies are needed. Here it is provided evidence that this assay is suitable for selecting patients for immunotherapy based on the administration of checkpoint inhibitors, as well as for monitoring the efficacy of checkpoint inhibitors in peripheral blood of cancer patients.

SUMMARY OF THE INVENTION

It is an object to provide an improved method for quantifying PD-L1 mRNA expression in a RNA sample such as an isolated RNA sample of CTCs in peripheral blood or fresh frozen tumor tissues of patients with solid tumors. The object is wholly or partially achieved by a method according to claim 1. Embodiments and further details of the invention are set of forth in the appended dependent claims, in the drawings and in the sequence listing. In particular the invention relates to an in vitro method for quantitative determination of the expression of Programmed Death Ligand 1 (PD-L1) mRNA in a sample, said method comprising the steps:

i. subjecting the sample to reverse transcription using RNA present in the sample as a template in order synthesize a corresponding cDNA sequence,
  ii. forming a reaction mixture comprising the sample, nucleic acid amplification reagents, a target primer pair, a target hydrolysis probe, said target primer pair and target hydrolysis probe being capable of hybridizing to PD-L1 mRNA,
  iii. subjecting the reaction mixture to amplification conditions optimized to generate at least one copy of a nucleic acid sequence complementary to a target sequence, said target sequence being a mRNA transcript of the PD-L1 mRNA sequence (SEQ ID NO: 1), and/or
  iv. determining the amount of PD-L1 mRNA in a said sample,
  v. normalizing the expression of PD-L1 with respect to an expression of a reference gene, and
  vi. comparing the amount of PD-L1 mRNA expressed in a said sample to a positive and negative control in order to estimate an overexpression of the PD-L1 mRNA sequence.

The method is based on the quantitative determination of PD-L1 mRNA expression in a sample. This assay may comprise a downstream analysis of PD-L1 mRNA expression in a RNA sample, such as an isolated RNA sample of CTCs in peripheral blood or fresh frozen tumor tissues of patients with solid cancers.

The CTCs isolation step could be performed by methods known to the skilled person, such as e.g. different microfluidic and filtration by size devices, density gradient centrifugation, positive and negative immunomagnetic selection, the CellSearch™ device, single cell analysis systems, or in-vivo CTC isolation systems such as the cell collector system (Gilupi, GmbH) or leukapheresis systems. It should be noted that CTC isolation is not limited to the listed methods.

In particular the target sequence in the method described herein is the mRNA-transcript of the PD-L1 gene, which is derived after reverse transcription of the RNA present in the sample by using a commercially available cDNA kit.

The quantification of PD-L1 mRNA expression may be used in many types of cancer such as breast, urothelial, colorectal, oesophageal, gastric, hepatocellular carcinoma, lung, melanoma, oropharyngeal squamous cell carcinoma, nasopharyngeal, multiple myeloma, renal cell carcinoma, cervical, glioblastoma, malignant mesotheliomas, lymphomas, ovarian and pancreatic. Advantageously, the quantification of PD-L1 mRNA expression may be used in any type of malignant neoplastic disease in order to quantify an expression of PD-L1 mRNA.

The method according to the invention amplifies specifically only the PD-L1 mRNA sequence, avoiding the amplification of genomic DNA. The method comprises a RT-qPCR, using a target primer pair, which comprises at least one intron-spanning site and a target hydrolysis probe. Advantageously the intron-spanning site may comprise only one base at either site of the intron resulting in that the target primers only bind to a sequence without introns under the conditions employed. The method utilizes a target primer pair that will only bind to a sequence in which the introns have been spliced-out, e.g. mRNA, cDNA. Moreover, the target hydrolysis probe is part of the amplification reaction mixture and hybridizes to the newly synthesized target sequence under select conditions, provided that this target sequence is present in the test sample.

According to the invention the main feature of the target primer pair is that it comprises at least one intron-spanning site. This provides a target primer pair that will only bind to a sequence in which the introns have been spliced out, e.g. mRNA, cDNA. It should be understood that said "splicing" may occur naturally i.e. to provide for the detection of mRNA in a biological sample. However, the term also encompasses an engineered sequence having the introns "spliced out" of the sequence, e.g. cDNA. The intron-spanning site may comprise only one base at either site of the intron provided that the target primer only binds the sequence without introns under the conditions employed. One or both of the forward and reverse target primers may comprise one or more intron-spanning site(s). In a preferred embodiment both target primers comprise an intron-spanning site.

In particular, the forward target primer is the primer that is extended in the same direction as the coding strand of the target nucleic acid. The forward target primer is designed to hybridize between exons 4 and 5 of the PD-L1 mRNA sequence in order to enhance only the mRNA target sequence avoiding DNA genomic amplification. The forward target primer is complementary to the 3'-end. Conversely, the reverse target primer is the primer that is extended in the same direction as the non-coding strand of the target nucleic acid. The reverse target primer is designed to hybridize between exons 5 and 6 of the PD-L1 mRNA sequence for amplification of only the target sequence avoiding non-specific products. Consequently, the target primers align with their 3'-ends facing each other.

More particularly, the "target primer pair", which is used in the method, is capable of hybridizing to a sequence of PD-L1 mRNA.

In particular the target sequence is the mRNA-transcript of the PD-L1 mRNA sequence (SEQ ID NO: 1). It should be noted that the DNA sequence for PD-L1 (SEQ ID NO: 1) listed in the enclosed sequence listings correspond to the transcribed mRNA sequence of said protein.

In a preferred embodiment the forward target primer should include at least the sequence 5'-TCATCCCAGAA-3' (SEQ ID NO: 3), more preferably the forward target primer includes the sequence 5'-GCTGAATTGGT-CATCCCAGAA-3' (SEQ ID NO: 4). In a preferred embodiment the reverse target primer should include at least the sequence 5'-CATTCTCCCTT-3' (SEQ ID NO: 5), more preferably the reverse target primer includes the sequence 5'-TTTCACATCCATCATTCTCCCTT-3' (SEQ ID NO: 6). The invention furthermore discloses sequences of specific probes, such as target hybridization probes, hydrolysis (TaqMan) probes or molecular Beacon, or SCORPION type probes, for detection/quantification of the amplification PCR product. Furthermore, the probe may be used to ensure specificity. Said probe is a target hydrolysis probe. Preferably the target hydrolysis probe should include at least the sequence 5'-GCACATCCTCCA-3' (SEQ ID NO: 7), more preferably the target hydrolysis probe includes the sequence 5'-6FAM-ACCTCTGGCACATCCTCCAAATGAAAG-BBQ-3' (SEQ ID NO: 8) and two fluorescent particles. The probes are preferably labelled. The label can be either directly detectable with for example fluorophores, chemiluminophores, fluorescent particles and the like or indirectly detectable with specific binding partners and nucleic acids. Preferred labels are directly detectable, and particular preferred labels are fluorescent dyes, such as SYBR Green I, FAM, HEX, VIC, fluorescein LC Red 610, LC Red640, LC Red670, LC Red 705, and other fluorescent dyes known in the art.

In particular, the target hydrolysis probe is designed to hybridize to an internal region within the amplicon. Especially, the target hydrolysis probe which is used in this method is designed to hybridize to an internal region of exon 5 of the PD-L1 mRNA sequence. It is typically a 20-30 bp oligonucleotide with a fluorescent reporter dye (i.e. 6-fluorescein, FAM) covalently attached to the 5' end and a fluorescent quencher dye (i.e. BlackBerry Quencher, BBQ). The proximally located quencher dye reduces the emission intensity of the reporter dye. The hydrolysis probe is added directly to the PCR mix, and conditions are virtually identical to those that are established for a standard PCR. During the extension phase of the PCR cycle, the Taq DNA polymerase cleaves the hydrolysis probe only when it is hybridized to the target, separating the reporter dye from the quencher dye. An increase in fluorescence intensity at 518 nm (when FAM is the reporter dye) (due to the release of the quenching effect on the reporter) is the result of hydrolysis probe hydrolysis and is quantitative for the initial amount of the template. The fluorescence intensity specific to the reporter dye increases because of its lack of proximity to the quencher dye. Repeated cycles of denaturation, annealing, and extension result in exponential amplification of the PCR product and of fluorescence intensity.

In another aspect, step (v) of the method may further comprise a reference primer pair that hybridizes to a reference mRNA sequence of a reference gene in order to ensure that amplifiable material is present in the test samples and in order to avoid false negative results.

A reference gene ideally should be stable, expressed in the cells and tissues of interest that do not show changes under the experimental conditions or disease state. These genes are used to normalize the mRNA levels of genes of interest before the comparison between different samples by the RT-qPCR. These reference genes are responsible for measuring and reducing the errors from variations among the samples, extraction and RNA quality and efficiency in cDNA synthesis, internal controls and the different experimental samples like in normal cells or tumor tissue. In the RT-qPCR method, an appropriate reference gene should be considered for accurate quantification of mRNA expression because the quantification cycle (Ca) of the target genes is compared to the $C_Q$ of the reference gene. The expression levels of the reference gene should remain constant between different cells types; otherwise the normalization to varying internal reference can result to increased errors. Several genes have been used as reference genes, including hypoxanthine phosphoribosyl transferase (HPRT), β2-microglobulin (B2M), glyceraldehyde 3-phosphate dehydrogenase (GAPDH) and β-actin (ACTB), 18S ribosomal RNA (18S rRNA), 28S ribosomal RNA (28S rRNA), α-tubulin (TUBA), albumin (ALB), ribosomal protein L32 (RPL32), TATA sequence binding protein (TBP), cyclophilin C (CYCC), Eelongation factor 1α (EFIA), RNA polymerase II (RPII) [Suzuki T, Higgins P J, Crawford D R. Control selection for RNA quantitation. Biotechniques, 2000; 29:332-7].

In a preferred embodiment, B2M used as a reference gene in this invention, and advantageously said reference primer pair was designed to hybridize to the B2M (Beta-2-Microglobulin) mRNA sequence (SEQ ID NO: 2).

Therefore, in another aspect of the invention provides a reference primer pair of the B2M mRNA sequence (SEQ ID NO: 2). It should be noted that the DNA sequence B2M (SEQ ID NO: 2) listed in the enclosed sequence listings correspond to the transcribed mRNA sequence of said protein. In a preferred embodiment the forward reference primer should include at least the sequence 5'-GCCGTGT-GAAC-3' (SEQ ID NO: 9), more preferably the forward reference primer includes sequence 5'-GCCTGCCGTGT-GAACCATGT-3' (SEQ ID NO: 10). In a preferred embodiment the reverse reference primer should include at least the sequence 5'-CTTCAAACCTC-3' (SEQ ID NO: 11), more preferably the reverse reference primer includes the sequence 5'-AAATGCGGCATCTTCAAACCTC-3' (SEQ ID NO: 12).

In the context of the present invention "reference primer pair" and "target primer pair" are not the same. In the context of the present invention the term "reference primer pair" is intended to mean a primer pair, which is capable of hybridizing to a sequence of a gene, which is ubiquitous to a given cell. More particularly, the "reference primer pair", which is used in the method, is capable of hybridizing to a sequence of B2M mRNA sequence. In other words a "reference primer pair" can be used as an internal control in a method or kit of the invention.

In Real-time RT-qPCR a hybridization probe for the quantification of B2M expression may be used as described previously in relation to the PD-L1 primer pair. In a preferred embodiment the reference hydrolysis probe should include at least the sequence 5'-CTCGATCCCAC-3' (SEQ ID NO: 13), more preferably the reference hydrolysis probe includes the sequence 5'-6FAM-CATGATGCTGCTTA-CATGTCTCGATCCCAC-BBQ-3' (SEQ ID NO: 14) and two fluorescent particles.

In further aspect the present document also relates to a method for:
  i. diagnosing and/or prognosing malignant neoplastic disease in a subject before immunotherapy with checkpoint inhibitors, and/or
  ii. predicting efficacy of treatment of malignant neoplastic disease in a subject before immunotherapy with checkpoint inhibitors, and/or
  iii. assessing outcome of treatment of malignant neoplastic disease in a subject during and after immunotherapy with checkpoint inhibitors, and/or
  iv. assessing the recurrence of malignant neoplastic disease in a subject during and after immunotherapy with checkpoint inhibitors,
    wherein said method comprises the quantification of the PD-L1 mRNA in a sample according to the steps for the in vitro method as described herein,
    wherein the subject is a human being, who suffers from a malignant neoplastic disease,
    wherein the checkpoint inhibitors may comprise the immune checkpoint blockade inhibitors, such as anti-PD-L1 inhibitors.

The in vitro method as described herein may advantageously be used for determining the amount of the PD-L1 mRNA in a sample for:
  i. diagnosing and/or prognosing malignant neoplastic disease in a subject before immunotherapy with checkpoint inhibitors, and/or
  ii. predicting efficacy of treatment of malignant neoplastic disease in a subject before immunotherapy with checkpoint inhibitors, and/or
  iii. assessing outcome of treatment of malignant neoplastic disease in a subject during and after immunotherapy with checkpoint inhibitors, and/or
  iv. assessing the recurrence of malignant neoplastic disease in a subject during and after immunotherapy with checkpoint inhibitors,
    wherein the sample analyzed may be a biological sample, and said biological sample may be obtained from a subject. Advantageously, the subject is a mammal such as a human being, who suffers from a malignant neoplastic disease.

The malignant neoplastic disease may be selected from the group consisting of breast, urothelial, colorectal, oesophageal, gastric, hepatocellular carcinoma, lung, nasopharyngeal, multiple myeloma, renal cell carcinoma, lymphomas, melanoma, oropharyngeal squamous cell carcinoma, cervical, glioblastoma, malignant mesotheliomas, ovarian and pancreatic cancer.

The in vitro method as described herein is advantageously used when the subject suffers from breast and non-small cell lung cancer.

When diagnosing and/or prognosing malignant neoplastic disease in a subject before immunotherapy with checkpoint inhibitors, the method comprises the steps of:
  a) performing the in vitro method for quantification of the PD-L1 mRNA in a sample as described herein,
  b) determining the amount of PD-L1 mRNA in a said sample,
  c) normalizing the expression of PD-L1 with respect to B2M expression, used as a reference gene,
  d) comparing the amount of PD-L1 mRNA detected in a said sample to a positive control and a negative control in order to estimate the over-expression of PD-L1, thereby deriving prognostic information.

The sample is advantageously obtained from a subject who is suffering from a malignant neoplastic disease and who has not been prescribed immunotherapy with checkpoint inhibitors. Further embodiments are wherein the positive control comprises peripheral blood mononuclear cells (PBMC) from healthy control samples since PBMC express as well PD-L1 at very low levels.

Thus, an indication of prognostic information is a relative change in the amount of PD-L1 mRNA in a said sample that identifies before immunotherapy with checkpoint inhibitors and may estimate the risk of future outcomes in an individual based on their clinical and non-clinical characteristics. In particular, a method of determining the prognosis as used herein refers to the prediction of the outcome of, or future course of, a subject. Prognosis includes the prediction of patient's survival. Moreover, prognosis may be used to predict the disease-free survival time of an individual, progression-free survival time, disease specific survival time, survival rate, or survival time. Prognostic testing may be undertaken with (e.g. at the same time as) the diagnosis of a previously undiagnosed cancerous condition, or may relate to an existing (previously diagnosed) condition.

When predicting efficacy of treatment of malignant neoplastic disease in a subject before immunotherapy with checkpoint inhibitors, the method comprises the steps of:
a) performing the in vitro method for quantification of the PD-L1 mRNA in a sample as described herein,
b) determining the amount of PD-L1 mRNA in a said sample,
c) normalizing the expression of PD-L1 with respect to B2M expression, used as a reference gene,
d) comparing the amount of PD-L1 mRNA detected in a said sample to a positive and a negative control in order to estimate the overexpression of PD-L1, thereby predicting efficacy of treatment of malignant neoplastic disease in a subject.

The sample is advantageously obtained from a subject who is suffering from a malignant neoplastic disease and who has not been administered checkpoint inhibitors as immunotherapy. Thus, the prediction is associated with the amount of overexpression of PD-L1 mRNA in a said sample that is identified before receiving immunotherapy with checkpoint inhibitors, such as anti-PD-L1 inhibitors and may indicate if the subject is likely to respond favourably to a treatment regimen, and can hence be used clinically to make treatment decisions by choosing the most appropriate treatment modality for any particular subject.

When assessing outcome of treatment of malignant neoplastic disease in a subject during and after immunotherapy with checkpoint inhibitors, the method comprises the steps of:
a) performing the in vitro method for the quantification of the PD-L1 mRNA in a sample as described herein,
b) determining the amount of PD-L1 mRNA in said sample,
c) normalizing the expression of PD-L1 with respect to B2M expression, used as a reference gene,
d) comparing the amount of PD-L1 mRNA detected in said sample to a positive control in order to estimate the overexpression of PD-L1,
e) repeating steps a) to d) at one or more time points during and after immunotherapy with checkpoint inhibitors of said subject, and wherein a change in relative amount of PD-L1 mRNA in said samples over time indicates the efficacy of treatment.

The sample is advantageously obtained from a subject who is suffering from a malignant neoplastic disease before and after said subject is being administered checkpoint inhibitors as immunotherapy. Thus, an indication of effective treatment is a relative change in decreasing amount of PD-L1 mRNA in a said sample relative a previous sample analyzed in the steps of repeating the method.

When assessing recurrence of malignant neoplastic disease in a subject during and after immunotherapy with checkpoint inhibitors, the method comprises the steps of:
a) performing the in vitro method for the quantification of the PD-L1 mRNA in a sample as described herein,
b) determining the amount of PD-L1 mRNA in a said sample,
c) normalizing the expression of PD-L1 with respect to B2M expression, used as a reference gene,
d) comparing the amount of PD-L1 mRNA detected in a said sample to a positive and negative control in order to estimate the overexpression of PD-L1,
e) repeating steps a) to d) at one or more time points during and after immunotherapy with checkpoint inhibitors of said subject, and wherein a change in relative amount of PD-L1 mRNA in said samples over time indicates the risk of recurrence.

Thus, an indication of recurrence is a relative change in increasing amount of PD-L1 mRNA in said samples that identify malignant neoplastic disease during immunotherapy with anti-PD-L1 inhibitors, i.e. an over-time increase in the amount of PD-L1 mRNA in a sample relative a previous sample analyzed in the steps of repeating the method.

The invention also relates to a kit for determining the amount of PD-L1 mRNA in a sample, the kit for the quantification of PD-L1 in a sample may also be used for:
i. determining the expression of PD-L1 mRNA in a sample, and/or
ii. diagnosing and/or prognosing malignant neoplastic disease in a subject before immunotherapy with checkpoint inhibitors, and/or
iii. predicting efficacy of treatment of malignant neoplastic disease in a subject before immunotherapy with checkpoint inhibitors, and/or
iv. assessing outcome of treatment of malignant neoplastic disease in a subject during and after immunotherapy with checkpoint inhibitors, and/or
v. assessing the recurrence of malignant neoplastic disease in a subject during and after immunotherapy with checkpoint inhibitors.

The kit may further comprise:
a forward target primer for determining the quantity of PD-L1 in a sample, said forward target primer comprising or consisting of at least the sequence 5'-TCATCCCAGAA-3' (SEQ ID NO:3), more preferably the forward target primer includes the sequence 5'-GCTGAATTGGTCATCCCAGAA-3'(SEQ ID NO: 4), and/or
a reverse target primer for determining the quantification of PD-L1 in a sample, said reverse target primer comprising or consisting of at least the sequence 5'-CATTCTCCCTT-3' (SEQ ID NO: 5), more preferably the reverse target primer includes the sequence 5'-TTTCACATCCATCATTCTCCCTT-3' (SEQ ID NO: 6), and/or
a hydrolysis target probe for determining the quantity of PD-L1 in a sample, said hydrolysis target probe comprising or consisting of at least the sequence 5'-6FAM-GCACATCCTCCA-BBQ-3' (SEQ ID NO: 7), more preferably the target hydrolysis probe includes the sequence 5'-6FAM-ACCTCTGGCACATCCTC-CAAATGAAAG-BBQ-3' (SEQ ID NO: 8) and two fluorescent particles (FAM, BBQ), and/or a forward reference primer for normalization the data for the quantification of PD-L1 in respect to the expression of B2M as a reference gene, said forward reference primer comprising or consisting of at least the sequence 5'-GCCGTGTGAAC-3' (SEQ ID NO: 9), more preferably the forward reference primer includes the sequence 5'-GCCTGCCGTGTGAACCATGT-3' (SEQ ID NO: 10), and/or a reverse reference primer for normalization the data for the quantification of PD-L1 in respect to the expression of B2M as a reference gene, said reverse reference primer comprising or consisting of at least the sequence 5'-CTTCAAACCTC-3' (SEQ ID NO: 11), more preferably the reverse reference primer includes the sequence 5'-AAATGCGGCATCTTCAAACCTC-3' (SEQ ID NO: 12), and/or a reference hydrolysis probe for normalization the data for the quantification of PD-L1 in respect to the expression of B2M as a reference gene, said reference hydrolysis probe comprising or consisting of at least the sequence 5'-6FAM-CTCGATCCCAC-BBQ-3' (SEQ ID NO: 13), more preferably the reference hydrolysis probe includes the sequence 5'-6FAM-CATGATGCTGCT-TACATGTCTCGATCCCAC-BBQ-3' (SEQ ID NO: 14) and two fluorescent particles (FAM, BBQ).

BRIEF DESCRIPTION OF FIGURES

FIG. 2: depicts the hybridization sites for primers and hydrolysis probe for the amplification of PD-L1 mRNA sequence. The primers—forward, reverse— and hydrolysis probe were depicted in bold and the exon-exon junction was depicted with a forward slash.

FIG. 3: depicts the hybridization sites for primers and hydrolysis probe for the amplification of B2M mRNA sequence. The primers—forward, reverse— and hydrolysis probe were depicted in bold and the exon-exon junction was depicted with a forward slash.

DEFINITIONS

Figure 1:
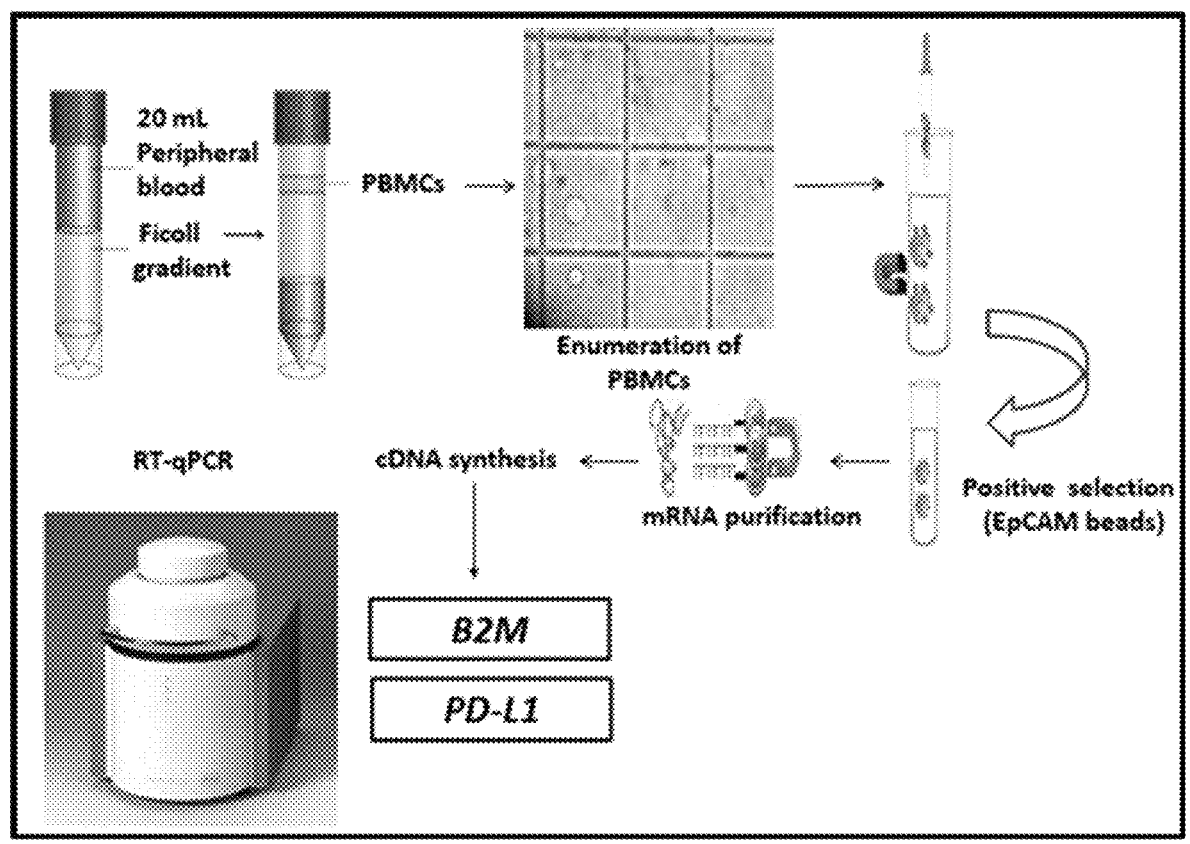
FIG. 1: illustrates the procedure for the isolation of CTCs from peripheral blood and down-stream RT-qPCR for PD-L1 and B2M.

The terms used in this invention are, in general, expected to adhere to standard definitions generally accepted by those having ordinary skill in the art of molecular biology. A few exceptions, as listed below, have been further defined within the scope of the present invention.

"At least one" as used herein means one or more, i.e. 1, 2, 3, 4, 5, 6, 7, 8, 9, 10 etc.

As used herein "target sequence" means a sequence that is detected, amplified, both amplified and detected or is complementary to the sequences provided herein or otherwise has at least one intron in its native state i.e. as genomic DNA or extra chromosomal DNA. While the term target sequence is sometimes referred to as single stranded, those skilled in the art will recognize that the target sequence may be double stranded. In particular, according to this text the "target sequence" is referred to the part of the PD-L1 sequence, which is amplified, when a primer pair binds to the desired sequence.

As used herein, the term "primer" refers to an oligonucleotide which, produced synthetically, is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase or the like, and at a suitable temperature and pH. The primer is preferably single stranded for maximum efficiency, but may alternatively be double stranded. If double stranded, the primer is first treated to separate its strands before being used to prepare extension products. The primer must be sufficiently long to prime the synthesis of extension products in the presence of the agents for polymerization. The exact lengths of the primers will depend on many factors, including temperature and the source of primer. For example, depending on the complexity of the target sequence, a primer typically contains 15 to 25 or more nucleotides, although it can contain fewer nucleotides. Short primer molecules generally require cooler temperatures to form sufficiently stable hybrid complexes with a template. In particular, the primers, which are used here, are preferably designed in a way that avoids amplification of genomic DNA or cDNA in order to avoid non-specific amplification of contaminating genomic DNA in the sample.

The optional reverse transcription step in the method of the invention is included wherever necessary in order to amplify the target sequence, i.e. when the nature of the target sequence is RNA. This process, designated reverse transcription, occurs under the direction of an RNA-dependent DNA polymerase enzyme called a reverse transcriptase. The process furthermore requires buffers and reagents, such as dNTPs, for the reverse transcription. Reverse transcription kits are commercially available, and it is within the skill to perform this process. The nucleic acid amplification reagents used in the invention includes reagents which are well known and may include, but are not limited to, an enzyme with polymerase activity e.g. heat stable polymerases such as the Taq-polymerase (and, as necessary, reverse transcriptase activity e.g. when monitoring mRNA), enzyme cofactors such as magnesium or manganese; salts and deoxynucleotide triphosphates (dNTPs).

The term "amplification conditions" is generally defined as conditions, which promote hybridizing or annealing of primer sequences to a target sequence and subsequent extension of the primer sequence. It is well known in the art that such annealing is dependent on several parameters, including temperature, ionic strength, sequence length, complementarity and G:C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures, which are close to (i.e. within 10'C) the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature. Once sequences are selected for a given diagnostic application, the G:C content and length will be known and can be accounted for in determining precisely what hybridization conditions will encompass. Since ionic strength is typically optimized for enzymatic activity the only parameter left to vary is the temperature. Generally, the hybridization temperature is selected close to or at the $T_m$ of the primers or probe. Thus, obtaining suitable hybridization conditions for a particular primer, probe, or primer and probe set is well within ordinary skill of one practicing this art. The amplification product produced as above can be detected during or subsequently to the amplification of the target sequence using any suitable method and a probe disclosed in greater detail below.

As used herein, the term "melting temperature" ($T_m$) in relation to an oligonucleotide is defined as the temperature at which 50% of the DNA forms a stable double-helix and the other 50% has been separated into single stranded molecules. As known to those of skill in the art, PCR annealing temperature is typically a few degrees less than the $T_m$, the latter of which is calculated based on oligo and salt concentrations in the reaction.

The terms "polynucleotide" and "oligonucleotide" are used interchangeably. "Oligonucleotide" is a term sometimes used to describe a shorter polynucleotide.

The terms "hybridized" and "hybridization" refer to the base-pairing interactions between two nucleic acids that result in formation of a duplex. It is not a requirement that two nucleic acids have 100% complementarity over their full length to achieve hybridization.

The term "external standard" as used herein means a synthetic DNA or RNA transcript in known amount(s) or concentration(s) that is tested separately from the test sample, i.e. through interpolation or extrapolation to a standard curve.

As used herein, "cycle threshold" (Ct) refers to quantification cycle values calculated from the record fluorescence measurements of the real time quantitative PCR. "Cq" refers to the number of cycles required for the PCR signal to reach the significant threshold. The calculated Cq value is proportional to the log of the number of target copies present in the sample. The Cq quantification is performed with any method for the real time quantitative PCR amplification described in the art [Bustin SA. Absolute quantification of mRNA using real-time reverse transcription polymerase chain reaction assays. J Mol Endocrinol 2000; 25: 169-193].

"Precision" is the measure of the degree of repeatability of an analytical method under normal operation and is normally expressed as the percent relative standard deviation for a statistically significant number of samples. The two most common precision measures are "repeatability" and "reproducibility". These are expression of two extreme measure of precision which can be obtained. Repeatability (the smallest expected precision) will give an idea of the sort of variability to be expected when a method is performed by a single analyst on one piece of equipment over a short time scale. If a sample is analyzed by a number of laboratories for comparative purposes then a more meaningful precision measure to use is reproducibility (this is the largest measure of precision).

"Limit of Detection" (LoD) is the lowest analyte concentration likely to be reliably distinguished from the blank and at which detection is feasible. LoD is determined by utilizing both the measured LoB and test replicates of a sample known to contain a low concentration of analyte.

"Limit of Quantification" (LoQ) refers to the lowest concentration at which the analyte can not only be reliably detected but at which some predefined goals for bias and imprecision are met. The LoQ is defined as three times the LOD.

"Linearity" is the ability of the method to elicit test results that are directly proportional to analyte concentration within a given range. Linearity is generally reported as the variance of the slope of the regression line. Traditionally linearity was regarded as a desirable property of methods as only linear curves could be easily interpreted. With the ready availability of computing power this is now of little importance and non-linear calibrations can readily be dealt with.

"False negative" refers to a test result indicates a subject does not suffer from a malignant neoplastic disease when the subject actually does have it. In the context of this application the "false negative" refers to a test result that is incorrect because the method failed to determine the overexpression of PD-L1 in a sample from a subject.

"False positives" refers to a test result that that indicates a subject who suffers from a malignant neoplastic disease when the subject actually does not have it. In the context of this application the "false positive" refers to a test result that is incorrect because the method indicates to determine the overexpression of PD-L1 in a sample, which does not exist.

"Healthy" refers to a subject possessing good health. Such a subject demonstrates an absence of any malignant or non-malignant disease. In the context of this application, a "healthy individual" is only healthy in that they have an absence of any malignant or non-malignant disease; a "healthy individual" may have other diseases or conditions that would normally not be considered "healthy".

"Prognosis" as used herein to refer to the prediction of the likelihood of progression, including recurrence, metastatic spread, and drug resistance, of a malignant neoplastic disease. For example, a patient having an expression profile, which correlates with an invasive phenotype, may exhibit a high proliferative activity, and therefore may be demonstrative of a favourable response to therapy, as the invasive phenotype can be a histologic characteristic used to indicate a therapy-sensitive neoplastic disease.

A "malignant" neoplasm is generally poorly differentiated (anaplasia), has characteristically rapid growth accompanied by progressive infiltration, invasion, and destruction of the surrounding tissue. Furthermore, a malignant neoplasm has the capacity to metastasize to distant sites. The term "metastasis" refers to the spread or migration of cancerous cells from a primary (original) tumor to another organ or tissue, and is typically identifiable by the presence of a "secondary tumor" or "secondary cell mass" of the tissue type of the primary (original) tumor and not of that of the organ or tissue in which the secondary (metastatic) tumor is located. For example, a carcinoma of the lung that has migrated to bone is said to be metastasized lung cancer, and consists of cancer cells originating from epithelial lung cells growing in bone tissue.

As used herein, the expression "clinical outcome" or "outcome" is meant to be expressed in terms of different endpoints such as Disease-Free Survival (DFS), Relapse-Free Survival (RFS), Time-to-Recurrence (TR), Cancer-Specific Survival (CSS) or Overall Survival (OS), in accordance with the recommendations of Punt C, Buyse M, Köhne C-H, Hohenberger P, Labianca R, Schmoll Hi, et al. Endpoints in Adjuvant Treatment Trials: A Systematic Review of the Literature in Colon Cancer and Proposed Definitions for Future Trials. J. Natl. Cancer Inst. 2007; 13: 998-1003.

As used herein, the expression "Relapse-Free Survival" or "Recurrence-Free Survival" (RFS) is defined as the time to any event, irrespective of the cause of this event, except for any second primary cancer. Recurrence of or death from the same cancer and all treatment-related deaths or deaths from other causes are events. Second primary from the same cancers and other primary cancers are ignored, and loss to follow-up is censored.

As used herein, the expression "Disease-Free Survival" (DFS) is defined as the time to any event, irrespective of the cause of this event. All events are included, except loss to follow-up which is censored.

As used herein, the "Overall Survival" (OS) is defined as the time to death, irrespective of cause, whether or not the death was due to cancer. Loco regional recurrence, distant metastases, second primary cancers, and second other primary cancers are ignored. Loss to follow-up is censored.

"Subject" as used herein includes humans, nonhuman primates such as chimpanzees and other apes and monkey species, farm animals such as cattle, sheep, pigs, goats and horses, domestic mammals such as dogs and cats, laboratory animals including rodents such as mice, rats and guinea pigs, and the like. The term does not denote a particular age or sex. Thus, adult and newborn subjects, as well as fetuses, whether male or female, are intended to be covered. In preferred embodiments, the subject is a mammal, including humans and non-human mammals. In the most preferred embodiment, the subject is a human.

As used herein a "biological sample" encompasses a variety of sample types obtained from any subject having or not having malignant neoplasm. A typical subject is a human. For example, biological samples include samples obtained from a tissue or blood fluids collected from an individual suspected of having a malignant neoplasm.

"Immunotherapy" is treatment that uses certain parts of a person's immune system to fight diseases such as cancer. This can be done either stimulating the immune system to work harder or smarter to attack cancer cells or giving the immune system components, such as man-made immune system proteins. Some types of immunotherapy are also sometimes called biologic therapy or biotherapy. In the last few decades immunotherapy has become an important part of treating some types of cancer. Immunotherapy includes treatments that work in different ways. Some boost the body's immune system in a very general way. Others help train the immune system to attack cancer cells specifically.

"Checkpoint inhibitors" (also known as immune checkpoint modulators) are designed to lessen the effectiveness of checkpoint proteins. They could have a variety of mechanisms of action, but if effective they let the immune system see the other molecules on the surface of the cancer cells. There are many kinds of immune checkpoint inhibitors, such as anti-PD-L1 inhibitors, anti-CTLA4 inhibitors etc.

As used herein the term circulating tumor cells (CTC) are cells that have shed into the vasculature from a primary tumor and circulate in the bloodstream. CTCs thus constitute seeds for subsequent growth of additional tumors (metastasis) in vital distant organs, triggering a mechanism that is responsible for the vast majority of cancer-related deaths.

As used herein, the term PD-L1 refers to the official name of the gene "Programmed death-ligand 1" (PD-L1; also called B7-H1 or CD274). The "Programmed death-ligand 1" gene is expressed on many cancer and immune cells and plays an important part in blocking the "cancer immunity cycle" by binding programmed death-1 (PD-1) and B7.1 (CD80), both of which are negative regulators of T-lymphocyte activation. Binding of PD-L1 to its receptors suppresses T-cell migration, proliferation and secretion of cytotoxic mediators, and restricts tumour cell killing. The PD-L1-PD-1 axis protects the host from overactive T-effector cells not only in cancer but also during microbial infections. Blocking PD-L1 should therefore enhance anticancer immunity, but little is known about predictive factors of efficacy. More especially, the term "target sequence", as used herein refers to PD-L1 mRNA sequence.

As used herein, the term B2M refers to the official name of the gene "beta-2-microglobulin", which encodes a serum protein found in association with the major histocompatibility complex (MHC) class I heavy chain on the surface of nearly all nucleated cells. The protein has a predominantly beta-pleated sheet structure that can form amyloid fibrils in some pathological conditions. The encoded antimicrobial protein displays antibacterial activity in amniotic fluid. More especially, the term "reference sequence", as used herein refers to B2M mRNA sequence.

As used herein, the term "reference gene" refers to any particular known genome sequence, whether partial or complete, of any organism or virus which may be used to reference identified sequences from a subject. For example, a reference genome used for human subjects as well as many other organisms is found at the National Center for Biotechnology Information at www.ncbi.nlm.nih.gov. A "genome" refers to the complete genetic information of an organism or virus, expressed in nucleic acid sequences. More especially, the term "reference gene", as used herein refers to B2M gene.

DETAILED DESCRIPTION

The present invention provides a highly sensitive, specific and reproducible real time RT-qPCR method for the quantification of PD-L1 expression in a biological sample, such as an isolated RNA sample from CTC in peripheral blood of patients with solid cancers or fresh frozen primary tumor tissues. The clinical importance of PD-L1 mRNA expression is associated with the response to targeted immunotherapies in many types of cancers.

Materials and Methods

Patients

As a first group, a total of 31 primary NSCLC carcinomas and their corresponding 31 adjacent non-neoplastic tissues were analyzed. As a second group, a total of 32 peripheral blood samples were obtained from 22 patients with metastatic breast cancer and 10 from healthy female blood donors, used as control group in order to define the specificity of the assay. The tissue samples were collected at the time of surgery and were immediately flash frozen in liquid nitrogen and stored at −80° C. All samples were analyzed histologically to access the account of tumor component (at least 70% of tumor cells) and the quality of material (i.e., absence of necrosis).

CTC Isolation from Peripheral Blood with Positive Immunomagnetic Selection

CTC were isolated from 20 mL peripheral blood as previously described [Strati A, et al. Gene expression profile of circulating tumor cells in breast cancer by RT-qPCR. BMC Cancer 2011; 11: 422]. This procedure is outlined in FIG. 1. Moreover, the developed RT-qPCR assay for PD-L1 can be applied in CTC samples isolated with different methodologies as well. To reduce blood contamination by epithelial cells from the skin, the first 5 ml of blood were discarded, and the collection tube was at the end disconnected before withdrawing the needle. After collection, peripheral blood was diluted with 20 mL phosphate buffered saline (PBS, pH 7.3) and peripheral blood mononuclear cells (PBMCs) were isolated by gradient density centrifugation using Ficol-Paque™ PLUS (GE Healthcare, Bio-Sciences AB) at 670 g for 30 min at room temperature. The interface cells were removed, washed twice with 40 mL of sterile PBS (pH 7.3, 4° C.), at 530 g for 10 min, and resuspended in 1 mL of PBS. CTC were enriched using immunomagnetic Ber-EP4 coated capture beads (Dynabeads® Epithelial Enrich, Invitrogen), according to manufacturer's instructions. Two fractions were isolated for each sample: the EpCAM-positive CTC fraction (CTC fraction) and the corresponding EpCAM-negative fraction containing the PBMC (PBMC fraction).

RNA Isolation from Tumor Tissues and cDNA Synthesis

Total cellular RNA was isolated with the Qiagen RNeasy Mini Reagent Set (Qiagen), according to the manufacturers' instructions. All preparation and handling steps of RNA took place in a laminar flow hood under RNase-free conditions. The isolated RNA was dissolved in RNA storage buffer (Ambion) and stored at −70° C. until use. RNA concentration was determined in the NanoDrop® ND-1000 spectrophotometer (NanoDrop Technologies). The amount of 1 µg of total RNA was used to perform reverse transcription of RNA with the High-Capacity RNA-to-cDNA™ Kit (Applied Biosystems, USA) in a total volume of 20 µL, according to the manufacturer's instructions.

RNA Isolation from CTCs and cDNA Synthesis

Total RNA isolation was performed using the TRIZOL-LS reagent (Invitrogen, USA). All RNA preparation and handling steps took place in a laminar flow hood, under RNAse-free conditions. The isolated RNA was dissolved in 20 µL of RNA storage buffer (Ambion, USA) and stored at −70° C. until use. RNA concentration was determined by absorbance readings at 260 nm using the Nanodrop-1000 spectrophotometer (NanoDrop, Technologies, USA). mRNA was isolated from the total RNA, using the Dynabeads mRNA Purification kit (Invitrogen, USA) according to the manufacturer's instructions. cDNA synthesis was performed using the High-Capacity RNA-to-cDNA™ Kit (Applied Biosystems, USA) in a total volume of 20 µL according to the manufacturer's instructions.

Primer and Probe Designs

Primers and hydrolysis probes for PD-L1 and B2M used as reference gene were de novo in-silico designed (Table 1). In-silico design was performed by using Primer Premier 5.0 software (Premier Biosoft, CA, USA) to avoid primer-dimer formation, false priming sites and formation of hairpin structures. Hybridization to genomic DNA was completely avoided. Moreover, the primers and probes were designed, so as to amplify specifically PD-L1 or B2M target genes according to the search in the BLAST Sequence Similarity Search tool (NCBI, NIH). The hydrolysis probes included a 5'-fluorescein (FAM) as a fluorophore covalently attached to the 5'-end of the oligonucleotide probe and a BlackBerry® Quencher (BBQ) as a quencher at the 3'-end. The position of primers and hydrolysis probes for each target gene are shown in FIGS. 2 and 3.

TABLE 1

RT-qPCR assay for PD-L1 and B2M expression; sequences of primers and hydrolysis probes

| Gene (Accession No) | Sequence (5'-3') | Tm (° C.) | Amplicon Size (bp) |
|---|---|---|---|
| PD-L1 (NM_014143) | | | |
| Target forward primer | 5'-GCTGAATTGGTCATCCCAGAA-3' (SEQ ID NO: 4), S1 | 59.8 | 147 |
| Target reverse primer | 5'-TTTCACATCCATCATTCTCCCTT-3' (SEQ ID NO: 6), S1 | 60.2 | |
| Hydrolysis target probe | 5'-6FAM-ACCTCTGGCACATCCTCCAAATGAAAG-BBQ-3' (SEQ ID NO: 8), S1 | 69.8 | |
| B2M (NM_004048) | | | |
| Reference forward primer | 5'-GCCTGCCGTGTGAACCATGT-3' (SEQ ID NO: 10), S2 | 63.7 | 99 |
| Reference reverse primer | 5'-AAATGCGGCATCTTCAAACCTC-3' (SEQ ID NO: 12), S2 | 63.2 | |
| Hydrolysis reference probe | 5'-6FAM-CATGATGCTGCTTACATGTCTCGATCCCAC-BBQ-3' (SEQ ID NO: 14), S2 | 73.4 | |

For each gene, a primer pair and a hydrolysis probe were designed. For PD-L1, a primer set S1 was designed to amplify the region (147 bp) that comprises at least one intron-spanning site. This provides a primer pair that will only bind to a sequence in which the introns have been spliced out, e.g. mRNA, cDNA. In particular, the forward primer is designed between exons 4 and 5 (intron exon junction) and the reverse primer is designed between exons 5 and 6 (intron exon junction) of PD-L1 mRNA sequence in order to enhance only the mRNA target sequence avoiding DNA genomic amplification and non-specific products. The hydrolysis probe is designed to hybridize to an internal region within the amplicon. For B2M, a primer pair and a hydrolysis probe were designed. For B2M, a primer set S2 was designed to amplify the region (99 bp) that comprises at least one intron-spanning site. This provides a primer pair that will only bind to a sequence in which the introns have been spliced out, e.g. mRNA, cDNA. In particular, the forward primer is designed in internal region of exon 9 of B2M mRNA sequence and the reverse primer is designed between exons 2 and 3 of B2M mRNA sequence for amplification only the target sequence avoiding non-specific products. In this case, the hydrolysis probe is designed to be hybridized between exons 3 and 4 (intron exon junction). All primers and probes sequences are shown in detail in Table 1.

RT-qPCR Assay

RT-qPCR reaction was performed in the LightCycler 2.0 (IVD instrument, Roche, Germany) using glass capillary tubes (Roche Applied Science, Germany). As positive control used PBMC from healthy control samples since PBMC express as well PD-L1. The cycling protocol was identical for both PD-L1 and B2M and consisted of an initial 2-min denaturation step at 95° C., followed by 45 cycles of denaturation at 95° C. for 10 s, annealing at 58° C. for 20 s, and extension at 72° C. for 20 s. Real-time-PCR was performed in a total volume of 10 µL per reaction. The PCR reaction mix for PD-L1 and B2M are described in detail IN Table 2.

TABLE 2

Reaction components for PD-L1 and B2M RT-qPCR

| | PD-L1 | | | B2M | | |
|---|---|---|---|---|---|---|
| Reagents | Initial conc | V (µL) | Final conc | Initial conc | V (µL) | Final conc |
| Buffer | 5X | 3 | 1.5X | 5X | 1 | 0.5X |
| Mg | 25 mM | 1 | 2.5 mM | 25 mM | 1.2 | 3 mM |
| dNTPs | 10 mM | 0.2 | 200 µM | 10 mM | 0.15 | 150 µM |
| BSA | 10 µg/µL | 0.6 | 0.6 µg/µL | 10 µg/µL | 0.3 | 0.3 µg/µL |
| Forward primer | 10 µM | 0.3 | 0.3 µM | 10 µM | 0.25 | 0.25 µM |
| Reverse primer | 10 µM | 0.3 | 0.3 µM | 10 µM | 0.25 | 0.25 µM |
| Hydrolysis Probe | 3 µM | 0.83 | 0.25 µM | 3 µM | 0.83 | 0.25 µM |
| Taq polymerase | 5 U/µL | 0.1 | 0.05 U/µL | 5 U/µL | 0.1 | 0.05 U/µL |
| Volume of reaction | — | 10 | — | — | 10 | — |

Example 1

Development and Analytical Validation of the Assay

Figure 4:
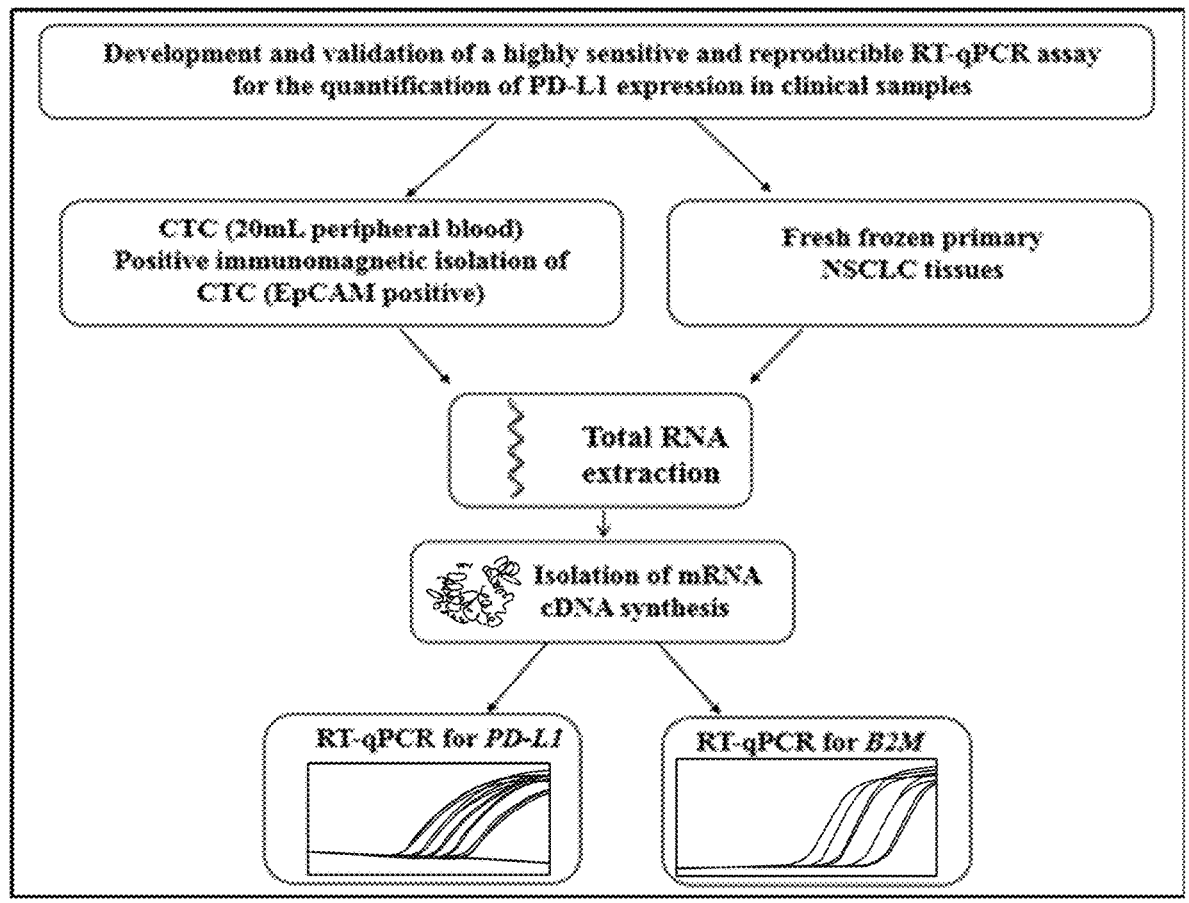
FIG. 4: RT-qPCR assay for PD-L1: experimental flowchart for PD-L1 mRNA expression in clinical samples.

The experimental flowchart of the study is outlined in FIG. 4.

Protocol optimization. A RT-qPCR based methods for the quantification of PD-L1 and 82M expression were optimized in a number of experiments, using as positive control cDNA samples from peripheral blood mononuclear cells (PBMC) of healthy control samples and negative control of PCR reaction mix, with respect to: PCR annealing temperature, cycling parameters, primers and probe concentrations, $Mg^{+2}$ and dNTPs concentrations.

Single RT-qPCR was performed for PD-L1 and B2M expression. Quantification is based on real-time monitoring during PCR of labelled specific hydrolysis probe for PD-L1. The cycle where the fluorescence signal rises above background noise (quantification cycle, Cq) is best quantified through the LightCycler software as the second derivative maximum of the curve.

Real-time RT-PCR for PD-L1 mRNA was performed using the LightCycler system (Roche Diagnostics). For the developed protocol, the primers and hydrolysis probes were used as previously described.

Real-time RT-PCR was performed in a total volume of 10 µL in the LightCycler glass capillaries. For the PCR, 1 µL of cDNA was placed into a 9 µL reaction volume containing a PCR reaction mix, which is described in Table 3. Moreover, the PCR conditions protocol was used as previously described.

The method can be also applied to any other real time PCR instrument, such as LightCycler 1.5 instrument, LightCycler 2.0 instrument, LightCycler 480 (Roche Diagnostics) and Applied Biosystems Real-Time PCR Instrument.

Example 2

RT-qPCR Quantification Using External Calibrators

Firstly, individual PCR amplicons specifically for PD-L1 and B2M were generated in order to be used as external quantification calibrators. For this purpose, total RNA was extracted from PBMC pool from normal samples since PBMC express as well PD-L1. cDNA was synthesized and served as a template for the amplification of PD-L1 and B2M by the above described RT-qPCR. PCR products were purified using MinElute PCR Purification Kit (Qiagen, Germany) and the amplicons were quantified in the Nanodrop-1000 spectrophotometer (NanoDrop, Technologies, USA).

DNA concentration was converted to copies/µL by use of the Avogadro number and the molecular weight of the amplicon number of bases of the PCR product multiplied by the mean molecular weight of a pair of nucleic acids which is 660. A standard stock solution corresponding to $10^{10}$ copies/µL for each gene transcript was prepared. Serial dilutions of this stock amplicon solution in DNase/RNase-free water ranging from $10^5$ copies/µL to 10 copies/µL served as quantification calibrators throughout the study. For the quantification of PD-L1 and B2M gene transcripts, an external calibration curve was obtained by plotting the concentration of each quantification calibrator expressed as copies/μL vs the corresponding quantification cycle (Cq).

Example 3

The Limit of Detection and Linearity of Assay

Figure 5:
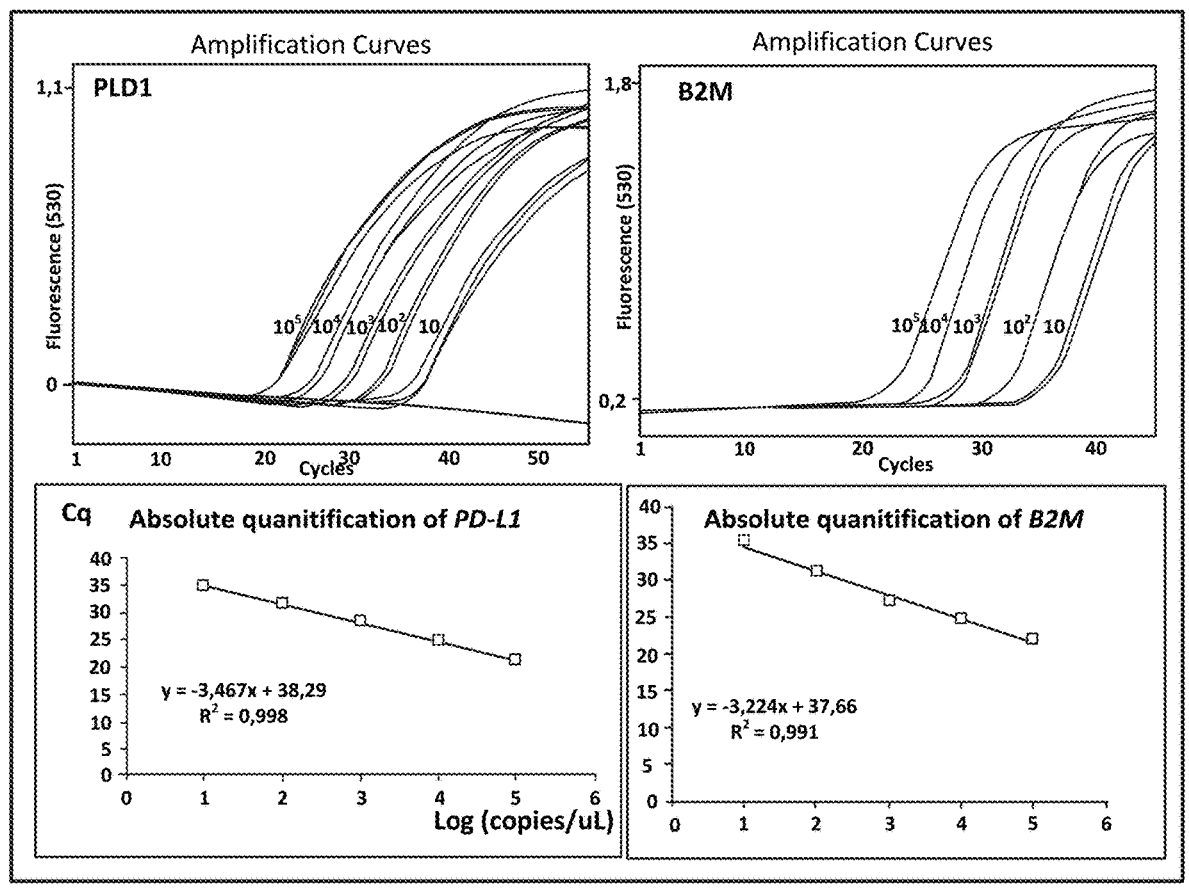
FIG. 5: presents the RT-qPCR calibration curves for PD-L1 and B2M (copies/μL, all measured in triplicate).

The limit of detection (LOD) of the developed RT-qPCR assay for both PD-L1 and B2M as copies/μL in the reaction was evaluated. To estimate LOD, the quantification calibrators containing a known number of copies/μL were prepared as described below in detail: For each gene target a calibration curve was generated using serial dilutions of these standards in triplicate for each concentration, ranging from 10s copies/μL to 10 copies/μL. The calibration curves showed linearity from 10 copies/μL up to $10^5$ copies/μL, with correlation coefficients larger than 0.99 in both cases, indicating a precise log-linear relationship (FIG. 5). None of the primers and hydrolysis probes gave any signal for any of the gene target transcripts when 50 ng/μL of 10 different genomic DNAs was analyzed.

The LOD for both of these assays was found to be 3 copies/μL and the limit of quantification (LOQ) was found to be 9 copies/μL, (estimated according to the MIQE Guidelines, S. Bustin et.al. Clin Chem. 2009). The characteristics of the calibration curves are given below in Table 3.

TABLE 3

Characteristics of the calibration curves for PD-L1 and B2M RT-qPCR

| Gene | mean slope n = 3 | Intercept n = 3 | PCR efficiency[a] (%) | LOD, copies/μL | LOQ, copies/μL |
|---|---|---|---|---|---|
| B2M | −3.237 + 0.013 | 37.67 + 0.031 | 104 | 3 copies/μL | 9 copies/μL |
| PD-L1 | −3.506 + 0.14 | 38.43 + 0.32 | 93 | 3 copies/μL | 9 copies/μL |

[a]PCR efficiency is expressed as E = $[10^{-1/slope}]-1$

Example 4

Evaluation of Intra and Inter-Assay Precision

Repeatability or intra-assay variance (within-run precision) of the PD-L1 RT-qPCR, was evaluated by repeatedly analyzing 3 cDNA samples corresponding to low, medium and high mRNA expression, while for B2M was evaluated by repeatedly analyzing 4 cDNA samples corresponding to 1, 10, 100 and 1000 cells equivalents per μL of cDNA in the same assay, in 3 parallel determinations.

Intra-assay variance expressed as the CVs (%) of the Cq variance for PD-L1, ranged from 0.84 to 1.2, while for B2M ranged from 0.21 to 0.72 (Table 4). Intra-assay variance expressed as within-run CVs of copies/μL ranged for PD-L1, from 16% to 20% and for B2M from 3.7% to 14% (Table 4). Reproducibility or inter-assay variance (between-run precision) of the RT-qPCR assays, was evaluated by analyzing the same cDNA sample, representing 100 SKBR-3 cells for B2M and PBMCs for PD-L1 and kept frozen in aliquots at −20° C., over a period of one month on 4 separate assays performed in 4 different days. Between-run CVs were 17% for B2M, and 15% for PD-L1 (Table 4).

TABLE 4

RT-qPCR for PD-L1 and B2M: Evaluation of intra and inter-assay precision

| B2M | Cq (SD) | CV % | Copies (SD) | CV % |
|---|---|---|---|---|
| SKBR-3 | Intra-assay precision (n = 3) | | | |
| 1 | 32.56 (0.11) | 0.34 | 3.8(±0.29)×10 | 7.9 |
| 10 | 29.29 (0.21) | 0.72 | 3.8 (±0.55)×$10^2$ | 14 |
| 100 | 25.79 (0.053) | 0.21 | 4.5 (±0.15)×$10^3$ | 3.7 |
| 1000 | 22.40 (0.10) | 0.45 | 4.9 (±0.36)×$10^4$ | 7.3 |
| | Inter-assay precision (n = 5) | | | |
| 100 PD-L1 | 25.73 (0.26) | 1.0 | 4.7 (±0.85)×$10^3$ | 17 |
| | Intra-assay precision (n = 3) | | | |
| cDNA 1 | 35.63 (0.30) | 0.84 | 6.5 (±1.3) | 20 |
| cDNA 2 | 31.48 (0.25) | 0.79 | 0.97 (±0.14) $10^2$ | 16 |
| cDNA 3 | 24.45 (0.29) | 1.2 | 1.0 (±0.18)×$10^4$ | 19 |
| | Inter-assay precision (n = 5) | | | |
| cDNA 4 | 29.57 (0.21) | 0.71 | 5.32 (±0.82)×$10^2$ | 15 |

Example 5

Normalization of Data for the Quantification of PD-L1 Expression in Primary Tumors and CTCs The normalization of data for the quantification of PD-L1 expression has performed in respect to the expression of B2M as a reference gene, and using the $2^{-\Delta\Delta Cq}$ method (Livak and Schmittgen, Methods 2001).

In primary tumors two samples were available for each patient: a) the primary tumor and the corresponding non-cancerous tissue. In this case for each sample, the expression of PD-L1 is estimated as a relative ratio to B2M used as a reference gene in both the primary tumor and its adjacent non-cancerous tissue, used as a calibrator. Then by using the $2^{-\Delta\Delta Cq}$ approach, the normalization of analytical signal (Cq) of PD-L1 in each primary tumor sample to the corresponding analytical signal (Cq) of PD-L1 in the adjacent non-cancerous sample.

In the case of CTCs for each sample, the expression of PD-L1 is estimated as a relative ratio to B2M used as a reference gene in both the EpCAM-positive CTC fraction and in the corresponding EpCAM-positive CTC fraction in the group of healthy blood donors used as a calibrator. Then by using the $2^{-\Delta\Delta Cq}$ approach, the overexpression of PD-L1 in the EpCAM-positive CTC fraction of peripheral blood samples was evaluated.

In the EpCAM-positive CTC fraction, one sample was defined as PD-L1 overexpressed based on the fold change of PD-L1 expression in respect to the group of ten healthy individuals used as a control group. More specifically, a cut-off value was estimated according to the expression of PD-L1 in the EpCAM-positive fraction of ten healthy individuals analysed in exactly the same way as the patient's peripheral blood samples. For these ten control samples, the difference of the Cq value ($\Delta Cq_{control}$) for PD-L1 from the respective Cq value for B2M ($Cq_{PD-L1}-Cq_{B2M}$) was measured. The median value of these 10 ΔCq values was 15.78±0.83 (Table 5).

TABLE 5

Expression of PD-L1 in PBMC (control group).
(ΔCq values: Cq $_{PD-L1}$-Cq $_{B2M}$)

| A/A | Cq PD-L1 | Cq B2M | ΔCq |
|---|---|---|---|
| 1 | 38.68 | 22.06 | 16.62 |
| 2 | 38.70 | 22.70 | 16.00 |
| 3 | 36.58 | 20.63 | 15.95 |
| 4 | 35.38 | 19.77 | 15.61 |
| 5 | 41.24 | 25.74 | 15.50 |
| 6 | 40.60 | 23.16 | 17.44 |
| 7 | 40.40 | 23.81 | 16.59 |
| 8 | 38.90 | 24.12 | 14.78 |
| 9 | 39.34 | 22.67 | 16.67 |
| 10 | 38.93 | 23.99 | 14.94 |
| | | SD | 0.83 |
| | | Median | 15.78 |
| | | Cut off | 14.70 |

Example 6

Expression of PD-11 in Primary Tumors (NSCLC)

Figure 6:
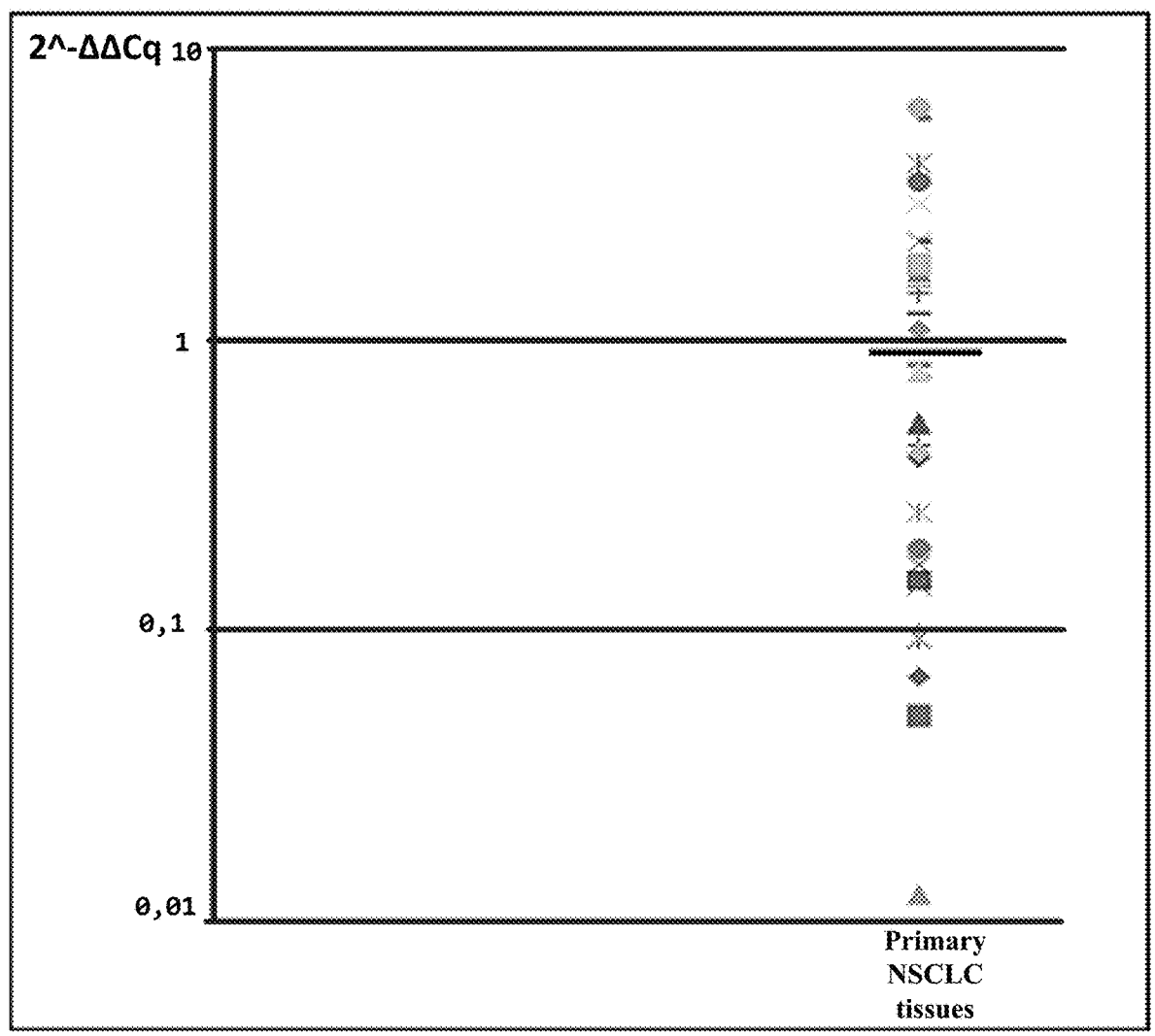
FIG. 6: shows the quantitative expression of PD-L1 in fresh frozen NSCLC primary tumors ($2^{-\Delta\Delta Cq}$ values).
Figure 7:
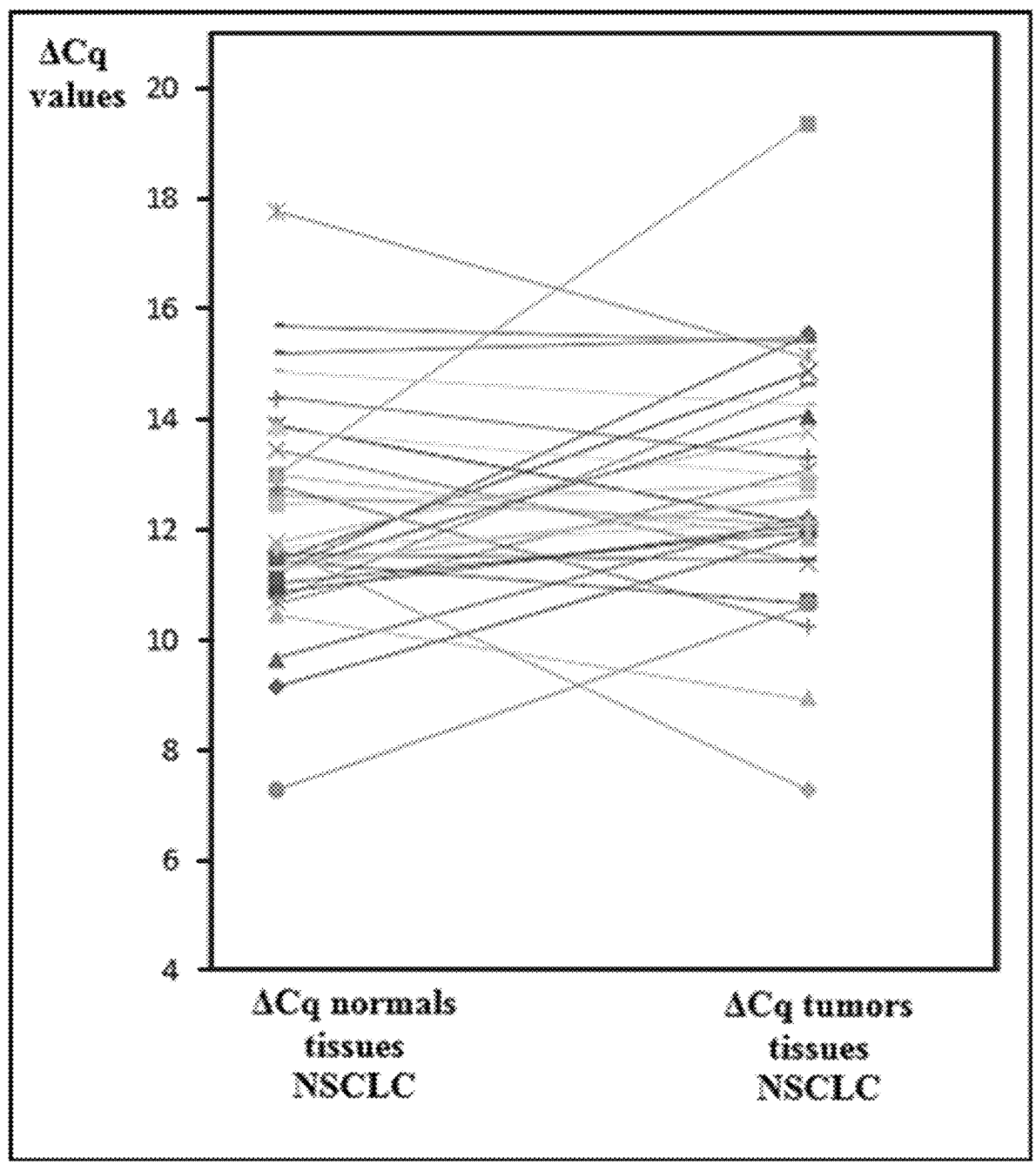
FIG. 7: shows the ΔCq values between primary tissues of NSCLC and their adjacent normals.

In this group, the quantification of PD-L1 expression was performed in 31 pairs of NSCLC tissues and their adjacent non-neoplastic tissues using RT-qPCR. PD-L1 was expressed in all tissues, and its expression was normalized with respect to B2M gene expression and by using the relative quantification approach described by Livak and Schmittgen as previously described. In this study demonstrated that PD-L1 was overexpressed in 14/31 (45.2%) of NSCLC tissues (FIG. 6). The ΔCq values between primary tissues of NSCLC and their adjacent normal samples are shown in FIG. 7.

Example 7

Expression of PD-L1 Expression in CTCs

In this group, the quantification of PD-L1 in the EpCAM-positive CTC fraction (isolated from peripheral blood from metastatic breast cancer patients) was performed. For each patient sample, the corresponding Cq$_{PD-L1}$-Cq$_{B2M}$ value (ΔCq$_{sample}$) was calculated. Then each individual ΔCq$_{sample}$ value was evaluated by finding its difference from the median ΔCq$_{control}$ value (ΔΔCq=ΔCq$_{sample}$−ΔCq$_{control}$) (Table 6). The median value of the $2^{-\Delta\Delta Cq}$ for the patients group analysed was 2.20. The samples with a $2^{-\Delta\Delta Cq}$ value above 2.20 or a ΔCq value below 14.7 were defined as positive for PD-L1 mRNA overexpression (Table 6). Moreover, the ΔCq values in all of the samples from healthy individuals were above 14.7 (FIG. 8).

Figure 8:
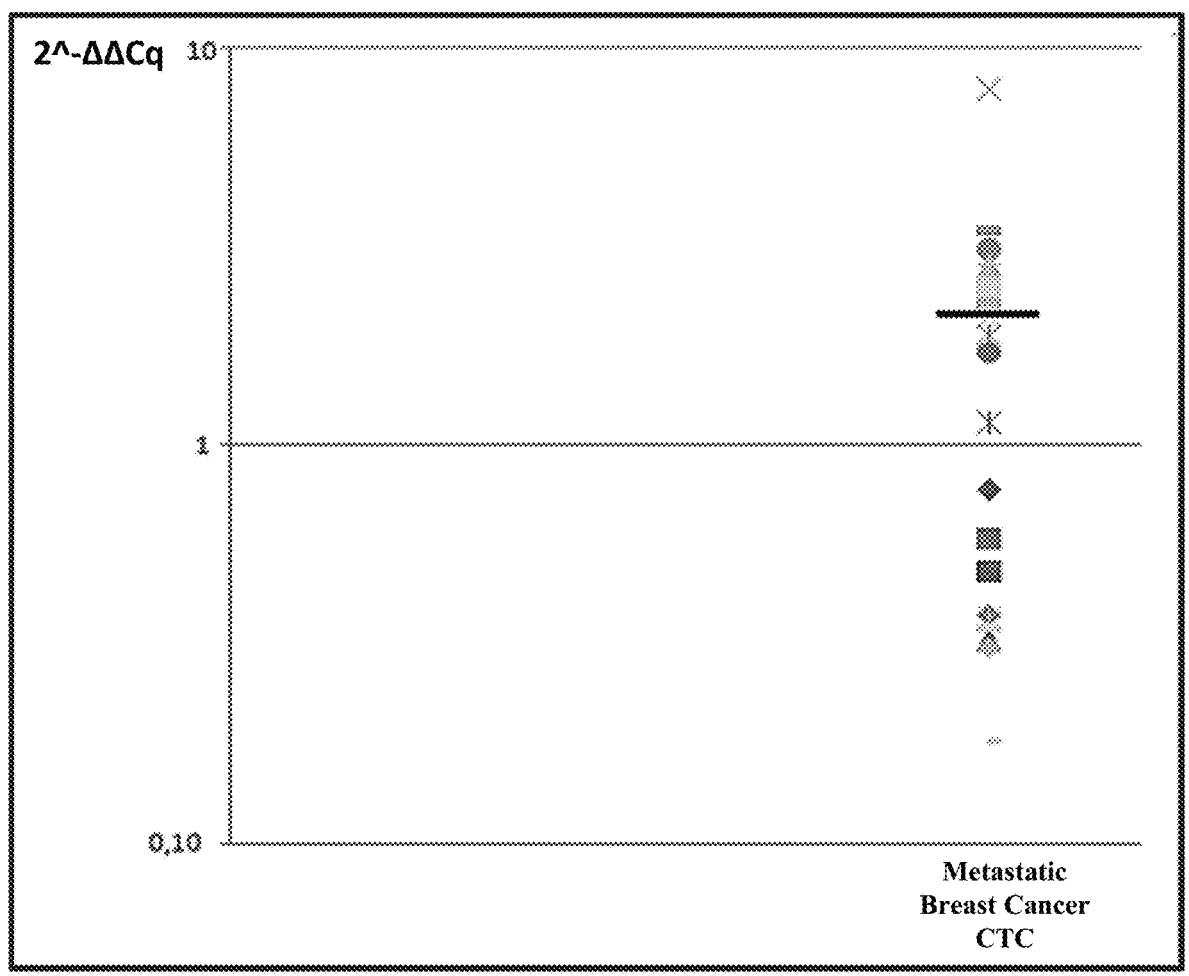
FIG. 8: shows the quantitative expression of PD-L1 in CTCs ($2^{-\Delta\Delta Cq}$ values).
Figure 9:
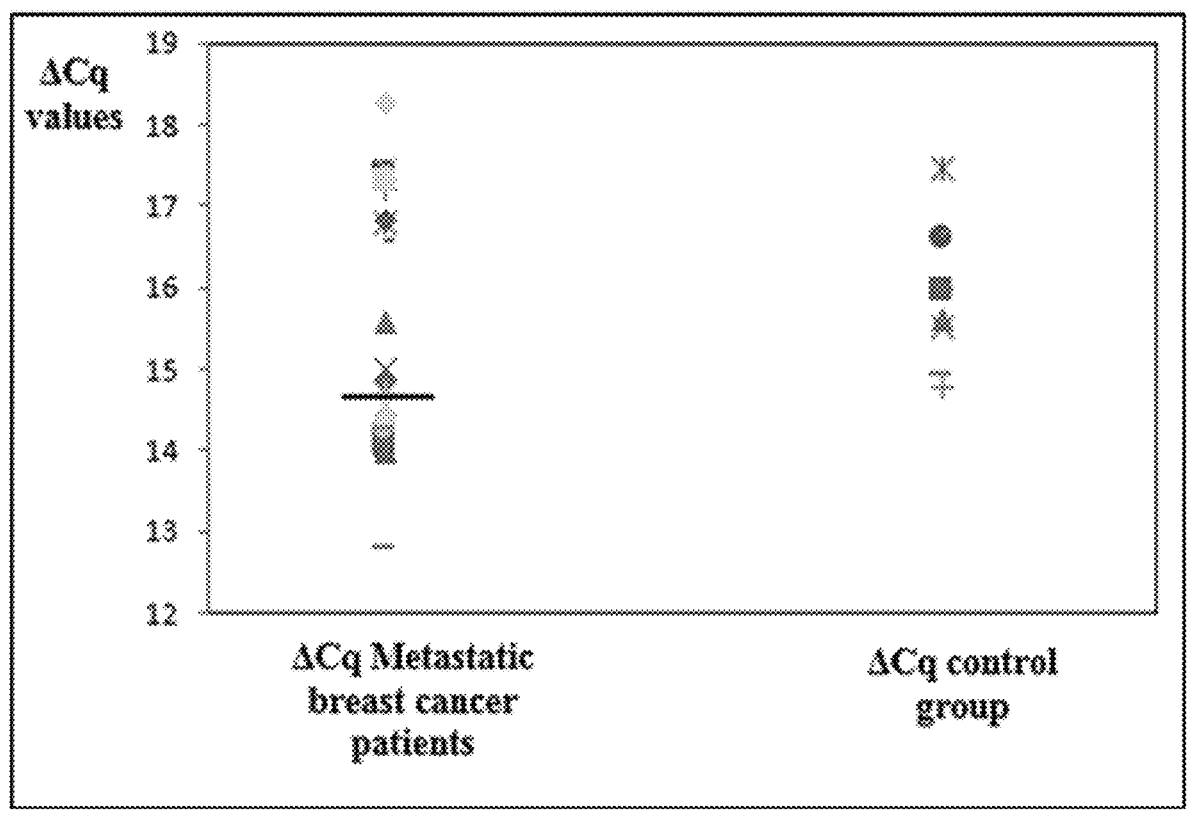
FIG. 9: shows the ΔCq values between control group and CTCs isolated from breast cancer metastatic samples.

According to the results, PD-L1 was found to be overexpressed in 8/22 (36.4%) patients with verified metastasis (FIG. 8). The ΔCq values between control group and CTCs isolated from breast cancer metastatic samples are shown in FIG. 9.

TABLE 6

Expression of PD-L1 in the EpCAM-positive
CTC fraction ($2^{-\Delta\Delta Cq}$ values)

| A/A | Cq PD-L1 | Cq B2M | ΔCq Cq$_{PD-L1}$ − Cq$_{B2M}$ | ΔΔCq ΔCq$_{sample}$ − ΔCq$_{control\ median}$ | $2^{-\Delta\Delta Cq}$ | Result |
|---|---|---|---|---|---|---|
| 1 | 38.47 | 22.32 | 16.15 | 0.37 | 0.77 | Negative |
| 2 | 36.32 | 19.49 | 16.83 | 1.05 | 0.48 | Negative |
| 3 | 38.71 | 21.31 | 17.40 | 1.62 | 0.33 | Negative |
| 4 | 37.51 | 21.92 | 15.59 | −0.19 | 1.14 | Negative |
| 5 | 39.24 | 24.24 | 15.00 | −078 | 1.72 | Negative |
| 6 | 39.52 | 22.74 | 16.78 | 1.00 | 0.50 | Negative |
| 7 | 34.81 | 20.82 | 13.99 | −1.79 | 3.46 | Positive |
| 8 | 40.39 | 23.2 | 17.19 | 1.41 | 0.38 | Negative |
| 9 | 38.45 | 21.89 | 16.56 | 0.78 | 0.58 | Negative |
| 10 | 34.89 | 22.09 | 12.8 | −2.98 | 7.89 | Positive |
| 11 | 36.10 | 21.25 | 14.85 | −0.93 | 1.91 | Negative |
| 12 | 39.30 | 25.16 | 14.14 | −1.64 | 3.12 | Positive |
| 13 | 38.63 | 24.66 | 13.97 | −1.81 | 3.51 | Positive |
| 14 | 40.98 | 23.51 | 17.47 | 1.69 | 0.31 | Negative |
| 15 | 35.78 | 21.21 | 14.57 | −1.21 | 2.31 | Positive |
| 16 | 38.86 | 24.58 | 14.28 | −1.5 | 2.83 | Positive |
| 17 | 39.26 | 24.55 | 14.71 | −1.07 | 2.10 | Negative |
| 18 | 38.57 | 21.35 | 17.22 | 1.44 | 0.37 | Negative |
| 19 | 39.82 | 25.54 | 14.28 | −1.5 | 2.83 | Positive |
| 20 | 39.23 | 20.97 | 18.26 | 2.48 | 0.18 | Negative |
| 21 | 38.82 | 21.51 | 17.31 | 1.53 | 0.35 | Negative |
| 22 | 35.37 | 20.91 | 14.46 | −1.32 | 2.50 | Positive |
| | | | | Median | 2.21 | |

What is claimed is:

1. An in vitro method for quantitative determination of the expression of Programmed Death Ligand 1 (PD-L1) mRNA in a sample, said method comprising:
   subjecting a sample to reverse transcription using RNA present in the sample as a template in order to synthesize a corresponding cDNA sequence;
   forming a reaction mixture comprising the sample, nucleic acid amplification reagents, a target primer pair, and a target hydrolysis probe, said target primer pair and target hydrolysis probe being capable of hybridizing to PD-L1 mRNA;
   subjecting the reaction mixture to amplification conditions optimized to generate at least one copy of a nucleic acid sequence complementary to a target sequence, said target sequence being a mRNA transcript of the PD-L1 mRNA sequence (SEQ ID NO: 1);
   determining the amount of PD-L1 mRNA in the sample;
   normalizing the expression of PD-L1 with respect to an expression of a reference gene; and comparing the amount of PD-L1 mRNA expressed in the sample to a positive and negative control in order to estimate an overexpression of the PD-L1 mRNA sequence;

wherein the forward PD-L1 target primer has a forward sequence of 5'-GCTGAATTGGTCATCCCAGAA-3' (SEO ID NO: 4); and wherein the reverse target primer of PD-L1 is designed to hybridize between exon 5 and 6 of the PD-L1 mRNA sequence and has a reverse sequence of 5'-TTTCACATCCATCATTCTCCCTT-3' (SEQ ID NO: 6).

2. The method according to claim 1, wherein the sample is a biological sample.

3. The method according to claim 2, wherein the biological sample comprises Circulating Tumor Cells (CTCs).

4. The method according to claim 3, wherein the biological sample is Circulating Tumor Cells (CTC) in peripheral blood or tumor tissue.

5. The method according to claim 1, wherein the target primer pair consists of a forward target primer and a reverse target primer, and wherein at least one of said forward or reverse target primers is capable of hybridizing to an intron spanning site of the target sequence.

6. The method according to claim 5, wherein the forward target primer is designed to hybridize between exon 4 and 5 of the PD-L1 mRNA sequence.

7. The method according to claim 1, wherein the target hydrolysis probe comprises fluorescent particles.

8. The method according to claim 7, wherein the fluorescent particles of the target hydrolysis probe comprise a fluorescent reporter covalently attached to the 5' end of the target hydrolysis probe and a fluorescent quencher dye attached to the 3' end.

9. The method according to claim 1, wherein the target hydrolysis probe comprises at least one sequence selected from 5'-GCACATCCTCCA-3' (SEQ ID NO 7) and 5'-ACCTCTGGCACATCCTCCAAATGAAAG-3' (SEQ ID NO: 8) and two fluorescent particles.

10. The method according to claim 1, wherein the reaction mixture further comprises a reference primer pair and a reference hydrolysis probe capable of hybridizing to a reference gene.

11. The method according to claim 10, wherein the reference gene is selected from the group consisting of hypoxanthine phosphoribosyl transferase (HPRT), β2-microglobulin (B2M), glyceraldehyde 3-phosphate dehydrogenase (GAPDH) and β-actin (ACTB), 18S ribosomal RNA (18S rRNA), 28S ribosomal RNA (28S rRNA), α-tubulin (TUBA), albumin (ALB), ribosomal protein L32 (RPL32), TATA sequence binding protein (TBP), cyclophilin C (CYCC), Eelongation factor 1α (EF1A), and RNA polymerase II (RPII).

12. The method according to claim 11, wherein the reference gene is β2-microglobulin (B2M) mRNA sequence (SEQ ID NO: 2).

13. The method according to claim 10, wherein the reference primer pair consists of a forward reference primer and a reverse reference primer.

14. The method according to claim 13, wherein the forward reference primer comprises at least one sequence selected from 5'-GCCGTGTGAAC-3' (SEQ ID NO: 9) and 5'-GCCTGCCGTGTGAACCATGT-3' (SEQ ID NO: 10).

15. The method according to claim 13, wherein the reverse reference primer comprises at least one sequence selected from 5'-CTTCAAACCTC-3' (SEQ ID NO: 11) and 5'-AAATGCGGCATCTTCAAACCTC-3' (SEQ ID NO: 12).

16. The method according to claim 10, wherein the reference hydrolysis probe comprises fluorescent particles.

17. The method according to claim 16, wherein the fluorescent particles of the reference hydrolysis probe comprise a fluorescent reporter covalently attached to the 5' end of the reference hydrolysis probe and a fluorescent quencher dye attached to the 3' end.

18. The method according to claim 10, wherein the reference hydrolysis probe comprises at least one sequence selected from 5'-CTCGATCCCAC-3' (SEQ ID NO: 13) and 5'-CATGATGCTGCTTACATGTCTCGATCCCAC-3' (SEQ ID NO: 14), and further comprises two fluorescent particles.

19. The method according to claim 1, wherein a positive control is a sample comprising PD-L1 mRNA.

20. The method according to claim 1, wherein a negative control is a sample devoid of PD-L1 mRNA.

21. The method according to claim 1, wherein the quantitative determination of PD-L1 mRNA is assayed by real time RT-qPCR.

* * * * *

```
                        SEQUENCE LISTING

<160> NUMBER OF SEQ ID NOS: 14

<210> SEQ ID NO 1
<211> LENGTH: 3691
<212> TYPE: DNA
<213> ORGANISM: Homo sapiens
<220> FEATURE:
<223> OTHER INFORMATION: PD-L1 mRNA sequence (NM_014143)

<400> SEQUENCE: 1
ggcgcaacgc tgagcagctg gcgcgtcccg cgcggcccca gttctgcgca gcttcccgag       60
gctccgcacc agccgcgctt ctgtccgcct gcagggcatt ccagaaagat gaggatattt      120
gctgtcttta tattcatgac ctactggcat ttgctgaacg catttactgt cacggttccc      180
aaggacctat atgtggtaga gtatggtagc aatatgacaa ttgaatgcaa attcccagta      240
gaaaaacaat tagacctggc tgcactaatt gtctattggg aaatggagga taagaacatt      300
```

```
attcaatttg tgcatggaga ggaagacctg aaggttcagc atagtagcta cagacagagg    360
gcccggctgt tgaaggacca gctctccctg ggaaatgctg cacttcagat cacagatgtg    420
aaattgcagg atgcaggggt gtaccgctgc atgatcagct atggtggtgc cgactacaag    480
cgaattactg tgaaagtcaa tgccccatac aacaaaatca accaaagaat tttggttgtg    540
gatccagtca cctctgaaca tgaactgaca tgtcaggctg agggctaccc caaggccgaa    600
gtcatctgga caagcagtga ccatcaagtc ctgagtggta agaccaccac caccaattcc    660
aagagagagg agaagctttt caatgtgacc agcacactga gaatcaacac aacaactaat    720
gagattttct actgcacttt taggagatta gatcctgagg aaaaccatac agctgaattg    780
gtcatcccag aactacctct ggcacatcct ccaaatgaaa ggactcactt ggtaattctg    840
ggagccatct tattatgcct tggtgtagca ctgacattca tcttccgttt aagaaaaggg    900
agaatgatgg atgtgaaaaa atgtggcatc caagatacaa actcaaagaa gcaaagtgat    960
acacatttgg aggagacgta atccagcatt ggaacttctg atcttcaagc agggattctc   1020
aacctgtggt ttaggggttc atcggggctg agcgtgacaa gaggaaggaa tgggcccgtg   1080
ggatgcaggc aatgtgggac ttaaaaggcc caagcactga aaatggaacc tggcgaaagc   1140
agaggaggag aatgaagaaa gatggagtca acagggagc ctggagggag accttgatac   1200
tttcaaatgc ctgaggggct catcgacgcc tgtgacaggg agaaaggata cttctgaaca   1260
aggagcctcc aagcaaatca tccattgctc atcctaggaa gacgggttga gaatccctaa   1320
tttgagggtc agttcctgca gaagtgcccct tgcctccac tcaatgcctc aatttgtttt   1380
ctgcatgact gagagtctca gtgttggaac gggacagtat ttatgtatga gttttcccta   1440
tttattttga gtctgtgagg tcttcttgtc atgtgagtgt ggttgtgaat gatttctttt   1500
gaagatatat tgtagtagat gttacaattt tgtcgccaaa ctaaacttgc tgcttaatga   1560
tttgctcaca tctagtaaaa catggagtat ttgtaaggtg cttggtctcc tctataacta   1620
caagtataca ttggaagcat aaagatcaaa ccgttggttg cataggatgt caccttttatt  1680 taacccatta atactctggt tgacctaatc ttattctcag acctcaagtg tctgtgcagt   1740
atctgttcca tttaaatatc agctttacaa ttatgtggta gcctacacac ataatctcat   1800
ttcatcgctg taaccaccct gttgtgataa ccactattat tttacccatc gtacagctga   1860
ggaagcaaac agattaagta acttgcccaa accagtaaat agcagacctc agactgccac   1920
ccactgtcct tttataatac aatttacagc tatattttac tttaagcaat tcttttattc   1980
aaaaaccatt tattaagtgc ccttgcaata tcaatcgctg tgccaggcat tgaatctaca   2040
gatgtgagca agacaaagta cctgtcctca aggagctcat agtataatga ggagattaac   2100
aagaaaatgt attattacaa tttagtccag tgtcatagca taaggatgat gcgaggggaa   2160 aaccccgagca gtgttgccaa gaggaggaaa taggccaatg tggtctggga cggttggata   2220
tacttaaaca tcttaataat cagagtaatt ttcatttaca aagagaggtc ggtacttaaa   2280
ataaccctga aaaataacac tggaattcct tttctagcat tatatttatt cctgatttgc   2340
ctttgccata taatctaatg cttgtttata tagtgtctgg tattgtttaa cagttctgtc   2400
ttttctattt aaatgccact aaattttaaa ttcataccct tccatgattc aaaattcaaa   2460
agatcccatg ggagatggtt ggaaaatctc cacttcatcc tccaagccat tcaagtttcc   2520
tttccagaag caactgctac tgcctttcat tcatatgttc ttctaaagat agtctacatt   2580
tggaaatgta tgttaaaagc acgtattttt aaaatttttt tcctaaatag taacacattg   2640
```

```
tatgtctgct gtgtactttg ctattttat ttattttagt gtttcttata tagcagatgg      2700
aatgaatttg aagttcccag ggctgaggat ccatgccttc tttgtttcta agttatcttt      2760
cccatagctt ttcattatct ttcatatgat ccagtatatg ttaaatatgt cctacatata      2820
catttagaca accaccattt gttaagtatt tgctctagga cagagtttgg atttgtttat      2880
gtttgctcaa aaggagaccc atgggctctc cagggtgcac tgagtcaatc tagtcctaaa      2940
aagcaatctt attattaact ctgtatgaca gaatcatgtc tggaactttt gttttctgct      3000
ttctgtcaag tataaacttc actttgatgc tgtacttgca aaatcacatt ttctttctgg      3060
aaattccggc agtgtacctt gactgctagc taccctgtgc cagaaaagcc tcattcgttg      3120
tgcttgaacc cttgaatgcc accagctgtc atcactacac agccctccta agaggcttcc      3180
tggaggtttc gagattcaga tgccctggga gatcccagag tttcctttcc ctcttggcca      3240
tattctggtg tcaatgacaa ggagtacctt ggctttgcca catgtcaagg ctgaagaaac      3300
agtgtctcca acagagctcc ttgtgttatc tgtttgtaca tgtgcatttg tacagtaatt      3360
ggtgtgacag tgttctttgt gtgaattaca ggcaagaatt gtggctgagc aaggcacata      3420
gtctactcag tctattccta agtcctaact cctccttgtg gtgttggatt tgtaaggcac      3480
tttatccctt ttgtctcatg tttcatcgta aatggcatag gcagagatga tacctaattc      3540
tgcatttgat tgtcactttt tgtacctgca ttaatttaat aaaatattct tatttatttt      3600
gttacttggt acaccagcat gtccattttc ttgtttattt tgtgtttaat aaaatgttca      3660
gtttaacatc ccagtggaga aagttaaaaa a                                    3691

<210> SEQ ID NO 2
<211> LENGTH: 987
<212> TYPE: DNA
<213> ORGANISM: Homo sapiens
<220> FEATURE:
<223> OTHER INFORMATION: B2M mRNA sequence (NM004048)

<400> SEQUENCE: 2
aatataagtg gaggcgtcgc gctggcgggc attcctgaag ctgacagcat tcgggccgag        60
atgtctcgct ccgtggcctt agctgtgctc gcgctactct ctctttctgg cctggaggct       120
atccagcgta ctccaaagat tcaggtttac tcacgtcatc cagcagagaa tggaaagtca       180
aatttcctga attgctatgt gtctgggttt catccatccg acattgaagt tgacttactg       240
aagaatggag agagaattga aaaagtggag cattcagact tgtctttcag caaggactgg       300
tctttctatc tcttgtacta cactgaattc acccccactg aaaaagatga gtatgcctgc       360
cgtgtgaacc atgtgacttt gtcacagccc aagatagtta agtgggatcg agacatgtaa       420
gcagcatcat ggaggtttga agatgccgca tttggattgg atgaattcca aattctgctt       480
gcttgctttt taatattgat atgcttatac acttacactt tatgcacaaa atgtagggtt       540
ataataatgt taacatggac atgatcttct ttataattct actttgagtg ctgtctccat       600
gtttgatgta tctgagcagg ttgctccaca ggtagctcta ggagggctgg caacttagag       660
gtggggagca gagaattctc ttatccaaca tcaacatctt ggtcagattt gaactcttca       720
atctcttgca ctcaaagctt gttaagatag ttaagcgtgc ataagttaac ttccaattta       780
catactctgc ttagaatttg ggggaaaatt tagaaatata attgacagga ttattggaaa       840
tttgttataa tgaatgaaac attttgtcat ataagattca tatttacttc ttatacattt       900
gataaagtaa ggcatggttg tggttaatct ggtttatttt tgttccacaa gttaaataaa       960
tcataaaact tgatgtgtta tctctta                                           987
```

```
<210> SEQ ID NO 3
<211> LENGTH: 11
<212> TYPE: DNA
<213> ORGANISM: Artificial Sequence
<220> FEATURE:
<223> OTHER INFORMATION: Forward target primer 1 (PD-L1)

<400> SEQUENCE: 3
tcatcccaga a                                                              11

<210> SEQ ID NO 4
<211> LENGTH: 21
<212> TYPE: DNA
<213> ORGANISM: Artificial Sequence
<220> FEATURE:
<223> OTHER INFORMATION: Forward target primer 2 (PD-L1)

<400> SEQUENCE: 4
gctgaattgg tcatcccaga a                                                   21

<210> SEQ ID NO 5
<211> LENGTH: 11
<212> TYPE: DNA
<213> ORGANISM: Artificial Sequence
<220> FEATURE:
<223> OTHER INFORMATION: Reverse target primer 1 (PD-L1)

<400> SEQUENCE: 5
cattctccct t                                                              11

<210> SEQ ID NO 6
<211> LENGTH: 23
<212> TYPE: DNA
<213> ORGANISM: Artificial Sequence
<220> FEATURE:
<223> OTHER INFORMATION: Reverse target primer 2 (PD-L1)

<400> SEQUENCE: 6
tttcacatcc atcattctcc ctt                                                 23

<210> SEQ ID NO 7
<211> LENGTH: 12
<212> TYPE: DNA
<213> ORGANISM: Artificial Sequence
<220> FEATURE:
<223> OTHER INFORMATION: Target hydrolysis probe 1 (PD-L1)

<400> SEQUENCE: 7
gcacatcctc ca                                                             12

<210> SEQ ID NO 8
<211> LENGTH: 27
<212> TYPE: DNA
<213> ORGANISM: Artificial Sequence
<220> FEATURE:
<223> OTHER INFORMATION: Target hydrolysis probe 2 (PD-L1)

<400> SEQUENCE: 8
acctctggca catcctccaa atgaaag                                             27

<210> SEQ ID NO 9
<211> LENGTH: 11
<212> TYPE: DNA
<213> ORGANISM: Artificial Sequence
<220> FEATURE:
```

<223> OTHER INFORMATION: Forward reference primer 1 (B2M)

<400> SEQUENCE: 9
gccgtgtgaa c    11

<210> SEQ ID NO 10
<211> LENGTH: 20
<212> TYPE: DNA
<213> ORGANISM: Artificial Sequence
<220> FEATURE:
<223> OTHER INFORMATION: Forward reference primer 2 (B2M)

<400> SEQUENCE: 10
gcctgccgtg tgaaccatgt    20

<210> SEQ ID NO 11
<211> LENGTH: 11
<212> TYPE: DNA
<213> ORGANISM: Artificial Sequence
<220> FEATURE:
<223> OTHER INFORMATION: Reverse reference primer 1 (B2M)

<400> SEQUENCE: 11
cttcaaacct c    11

<210> SEQ ID NO 12
<211> LENGTH: 22
<212> TYPE: DNA
<213> ORGANISM: Artificial Sequence
<220> FEATURE:
<223> OTHER INFORMATION: Reverse reference primer 2 (B2M)

<400> SEQUENCE: 12
aaatgcggca tcttcaaacc tc    22

<210> SEQ ID NO 13
<211> LENGTH: 11
<212> TYPE: DNA
<213> ORGANISM: Artificial Sequence
<220> FEATURE:
<223> OTHER INFORMATION: Reference hydrolysis probe 1 (B2M)

<400> SEQUENCE: 13
ctcgatccca c    11

<210> SEQ ID NO 14
<211> LENGTH: 30
<212> TYPE: DNA
<213> ORGANISM: Artificial Sequence
<220> FEATURE:
<223> OTHER INFORMATION: Reference hydrolysis probe 2 (B2M)

<400> SEQUENCE: 14
catgatgctg cttacatgtc tcgatcccac    30